(12) United States Patent
Saigo et al.

(10) Patent No.: US 8,710,263 B2
(45) Date of Patent: *Apr. 29, 2014

(54) ORGANIC SEMICONDUCTOR COMPOUND, SEMICONDUCTOR DEVICE, SOLAR CELL AND PRODUCING METHOD OF ORGANIC SEMICONDUCTOR COMPOUND

(71) Applicant: National Institute for Materials Science, Tsukuba (JP)

(72) Inventors: Kazuhiko Saigo, Kochi (JP); Yuka Kobayashi, Tokyo (JP)

(73) Assignee: National Institute for Materials Science, Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,310

(22) Filed: Jun. 25, 2013

(65) Prior Publication Data

US 2014/0012017 A1    Jan. 9, 2014

Related U.S. Application Data

(62) Division of application No. 12/867,821, filed as application No. PCT/JP2009/052440 on Feb. 15, 2009, now Pat. No. 8,501,801.

(30) Foreign Application Priority Data

Feb. 15, 2008    (JP) ................................ 2008-035311

(51) Int. Cl.
    *C07C 391/00*    (2006.01)

(52) U.S. Cl.
    CPC .................... *C07C 391/00* (2013.01)
    USPC ..................................................... 562/899

(58) Field of Classification Search
    USPC ..................................................... 562/899
    See application file for complete search history.

(56) References Cited

FOREIGN PATENT DOCUMENTS

| JP | 2-40378 | 2/1990 |
|----|---------|--------|
| JP | 2-258776 | 10/1990 |
| JP | 2-258777 | 10/1990 |
| JP | 2-258778 | 10/1990 |
| JP | 9-227552 | 9/1997 |
| JP | 2002-265466 | 9/2002 |
| JP | 2005-112951 | 4/2005 |
| JP | 2006-278692 | 10/2006 |
| JP | 2007-526640 | 9/2007 |

OTHER PUBLICATIONS

Liu, W. et al., "Syntheses, Electrochemical studies and Crystal Structures of New Unsymmetrical Tetrathiafulvalene Carboxylate Derivatives", Journal of Heterocyclic Chemistry (2007), vol. 44, pp. 831-836.

Enozawa H. et al., "Self-assembly and Solvatochromic Fiber Formation of 4,5-Bis(dodecylthio)tetrathiafulvalene-4'-carboxylic Acid and Its Derivatives", Chemistry Letters (2007), vol. 36, No. 12, pp. 1434-1435.

Parg, Roland P. et al., "A Semiconducting Langmuir-Blodgett Film of a Non-amphiphilic Bis-tetrathiafulvalene Derivative", Journal of Materials Chemistry (1995), vol. 5, No. 10, pp. 1609-1615.

Yamada, Yuri et al., "Suiso Ketsugo ni yori Renketsu sareta Π Kyoyaku Kessho no Sosei to Bussei Yosoku", Preprints of 84th Annual Meeting on Chemical Society of Japan in Spring 2004 Koen Yokoshu II, p. 1289.

Yamada, Yuri et al., "Suiso Ketsugo ni yori Renketsu sareta Π Kyoyaku Kessho no Sosei", Preprints of 85th Annual Meeting on Chemical Society of Japan in Spring 2005 Koen Yokoshu II, p. 1155.

Kaufman, Frank B., "Pi-Donor Intercalate Polymers: Synthesis, Charge-Transfer Interactions, and Applications", IBM J. Res. Develop. (1981), vol. 25, No. 4, pp. 303-314.

Yoshioka, Mayu et al., "Suiso Ketsugo ni yori Shuseki shita Tetrathiafulvalene Yudotai no Kozo to Bussei", Preprints of 88th Annual Meeting on Chemical Society of Japan in Spring 2008 Koen Yokoshu II, p. 1357.

Abstract of International Publication No. WO 2005/086251 A2, dated Sep. 15, 2005.

International Search Report mailed Mar. 17, 2009 in related International Application No. PCT/JP2009/052440.

King, Med. Chem. Principle and Practice (1994), pp. 206-208, XP002033086.

U.S. Office Action mailed Aug. 31, 2012 in related U.S. Appl. No. 12/867,821.

U.S. Office Action mailed Feb. 1, 2013 in related U.S. Appl. No. 12/867,821.

Lin et al: "A water-soluble derivative of tetrathiafulvalene exhibiting pH sensitive redox properties", New Journal of Chemistry, vol. 29, No. 3, Jan. 1, 2005, p. 509.

Fabre et al., Synthesis and Electrical Properties of Two New Conducting Materials Containing Unsymmetrical Tetraselenafulvalenes, Synthetic Metals, Elsevier Sequoia, Lausanne, vol. 13, No. 4, Feb. 1, 1986, pp. 339-343.

Supplementary European Search Report mailed Dec. 12, 2012 in related EP Patent Application No. EP09710791.

*Primary Examiner* — Taofiq A Solola

(74) *Attorney, Agent, or Firm* — Scully, Scott, Murphy & Presser, P.C.

(57) ABSTRACT

There is provided a compound or the like which can become a material in which many functions are controllable. A first aspect of the present invention lies in an organic semiconductor compound, characterized in that an organic molecule which becomes a donor is formed by being salt-formed with an inorganic acid or an inorganic base and self assembly is accomplished. According to this configuration, there can be obtained an organic semiconductor compound by a simple technique. A second aspect of the present invention lies in an organic compound, characterized in that a compound containing a tetrathiafulvalene affinity region in a framework thereof and having a protic acid functional group is formed by being induced to a salt with ammonia or a salt with hydroxyamine. According to this configuration, there can be obtained an organic compound in which many functions are controllable.

4 Claims, 21 Drawing Sheets

ORGANIC SEMICONDUCTOR COMPOUND, SEMICONDUCTOR DEVICE, SOLAR CELL AND PRODUCING METHOD OF ORGANIC SEMICONDUCTOR COMPOUND

RELATED APPLICATIONS

This application is a divisional application of U.S. patent application Ser. No. 12/867,821, filed on Oct. 26, 2010, which is a national stage entry of PCT Application No. PCT/JP2009/052440 filed on Feb. 15, 2009, which claims priority of Japanese Patent Application No. JP2008-035311 filed on Feb. 15, 2008, the entire content of each of which is incorporated by reference.

TECHNICAL FIELD

The present invention relates to an organic compound and particularly to an organic semiconductor compound, a semiconductor device, a solar cell and a producing method of an organic semiconductor compound.

BACKGROUND ART

Si-based amorphous semiconductors occupy the majority of the market presently due to the excellent workability thereof. For example, there is used an Si-based amorphous semiconductor frequently for a TFT (Thin Film Transistor) of a liquid crystal display or for a solar cell.

On the other hand, it is expected for the organic semiconductor to be applied to a wearable device because of such characteristics referred to as lightweight and flexibility. However, with respect mainly to the semiconductor portion, crystal or doped polymer is the mainstream and even when taking a consideration globally, the current situation is in that the development of organic semiconductors such as an organic amorphous semiconductor and the like are remarkably delayed.

Also, there are presently promoted developments of an organic thin film solar cell and an organic EL (Organic Electro-Luminescence) device, which use a low molecule it compound and a photoconductivity-doped polymer, but it is well known that the performances thereof are worse compared with that of an inorganic Si-based amorphous solid. This is related to a fact that high performance or stability cannot be maintained in the processing mode of a thin film, a chip or the like. Similarly as the inorganic Si-based amorphous which has high performance without relying upon the processing mode, it is expected for the organic compound of an organic amorphous solid or the like to have a high potential from an industrial viewpoint, but there are very few examples up to now in which it was applied. That is because the devices known as organic amorphous solids are limited to similar it electronic system starburst molecule groups in which there exist devices expressing conductivity on the radical bodies thereof, but the value thereof is generally very low.

Further, a general organic conductor of a charge transfer type is produced by an electrolysis method or the like, so that it is difficult to control molecular arrangement. Also, the electronic material property is largely dependent on the crystal structure, so that there is difficulty also in a viewpoint of the application to the thin film by polymerization and liquid crystallization which are needed for industrialization.

Also, for the conductive polymer which is made to be a semiconductor by executing a doping, it is difficult to control the arrangement thereof, so that it is difficult for the charge separation capability to be improved. Also, it lacks in chemical stability and the time degradation thereof is terrific.

InSc and GaAs crystals which have high Hall effect are rare metals and therefore, they are expensive and also lack in workability. Lightweight forming or thin-film forming is difficult also for a cobalt oxide crystal which is known as a thermoelectronic material.

Patent Document 1: Japanese unexamined patent publication No. 2005-112951

Patent Document 2: Japanese unexamined PCT patent publication No. 2007-526640

DISCLOSURE OF THE INVENTION

Problem to be Solved by the Invention

The present invention was invented in view of the background art mentioned above and has an object for providing a compound or the like that can become a material in which many functions are controllable.

Means for Solving the Problem

According to the present invention, in order to achieve the object mentioned above, there are employed configurations just described in the patent claims. Hereinafter, this invention will be explained in detail.

A first aspect of the present invention lies in an organic semiconductor compound, characterized in that an organic molecule which becomes a donor is formed by being salt-formed with an inorganic acid or an inorganic base and self assembly is accomplished.

According to this configuration, there can be obtained an organic semiconductor compound by a simple technique.

A second aspect of the present invention lies in the organic semiconductor compound according to claim 1, characterized by including an ammonium group.

According to this configuration, there can be obtained an organic semiconductor compound in which thermal electromotive force is generated by a mechanism derived from rotating and vibrating motions of an ammonium group.

A third aspect of the present invention lies in the organic semiconductor compound according to claim 2, characterized in that a hydrogen bonding is applied with respect to the ammonium group in a state of being self assembled.

According to this configuration, there can be obtained an organic semiconductor compound which is excellent in electronic conductivity.

A fourth aspect of the present invention lies in an organic compound, characterized in that a compound containing a tetrathiafulvalene affinity region in a framework thereof and having a protic acid functional group is formed by being induced to an ammonium salt or a hydroxyammonium salt.

According to this configuration, there can be obtained an organic compound in which many functions are controllable.

A fifth aspect of the present invention lies in an organic compound, characterized in that a compound containing a tetrathiafulvalene affinity region in a framework thereof and having a first class amine is formed by being induced to a salt with an inorganic acid.

According to this configuration, there can be obtained an organic compound in which many functions are controllable.

A sixth aspect of the present invention lies in an organic compound, characterized by being any one of the compounds expressed by the following Chemical Formulas 1.

[Chemical Formulas 1]

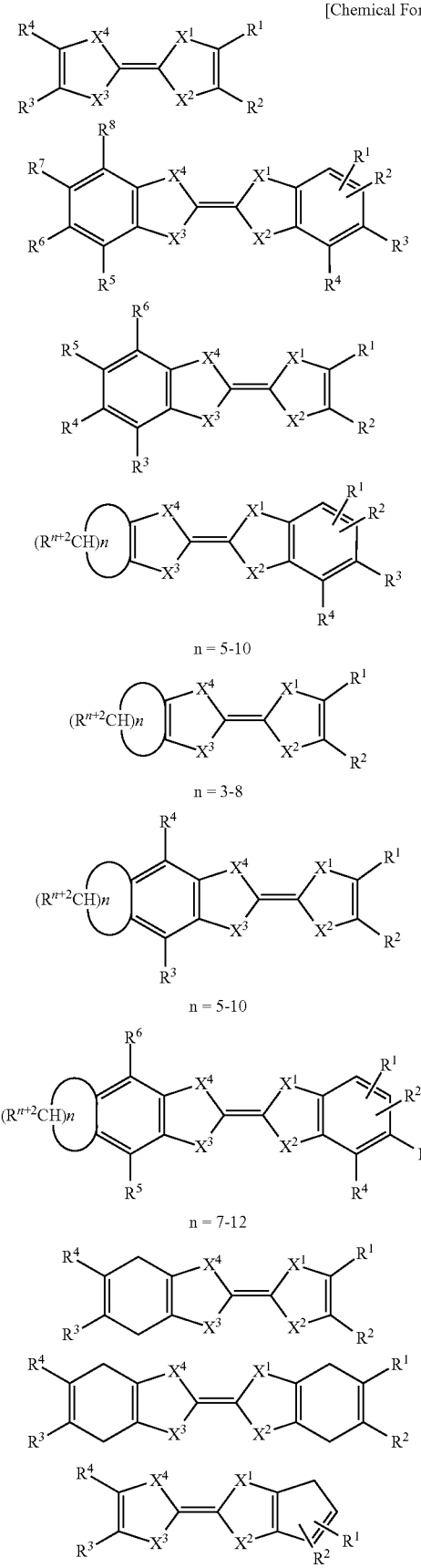

n = 5-10 n = 3-8 n = 5-10 n = 7-12

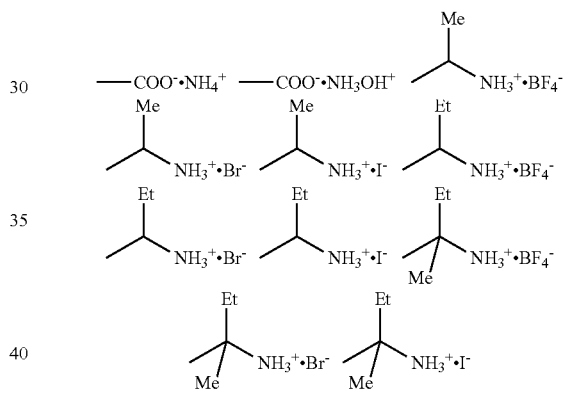

(In the formulas, $X^1$ to $X^4$ is S or Se, and $R^1$ is any one expressed in the following Chemical Formulas 2.)

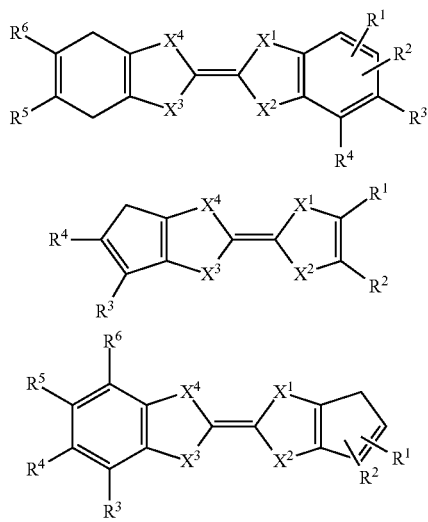

According to this configuration, there can be obtained an organic compound in which many functions are controllable.

A seventh aspect of the present invention lies in the organic compound according to claim 6, characterized in that $R^2$ to $R^8$ in the Chemical Formulas 1 are any one expressed in the following Chemical Formulas 3 (it is allowed for them to be identical or different).

[Chemical Formulas 3]

H, $ClH_m$ (l = 1~30, m = 3~61), $SClH_m$ (l = 1~30, m = 3~61), $OClH_m$ (l = 1~30, m = 3~61), $S(CH_2S)lCH_3$ (l = 1~20)

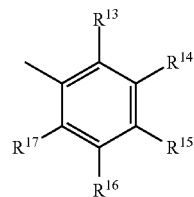

$R^{13}$~$R^{17}$ = H, $ClH_m$ (l = 1~30, m = 3~61), $SClH_m$ (l = 1~30, m = 3~61), $OClH_m$ (l = 1~30, m = 3~61), $S(CH_2S)lCH_3$ (l = 1~20)

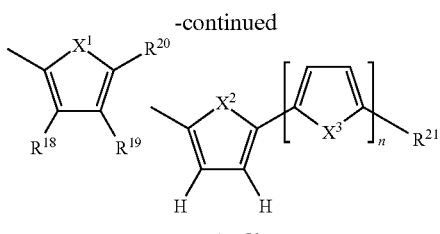

n = 1 ~ 50
$R^{18} \sim R^{21}$ = H, ClHm (l = 1~30, m = 3~61), SClHm (l = 1~30, m = 3~61), OClHm (l = 1~30, m = 3~61), S(CH$_2$S)lCH$_3$ (l = 1~20)

According to this configuration, there can be obtained an organic compound in which many functions are controllable.

An eighth aspect of the present invention lies in an organic compound characterized by being either one of the compounds expressed by the following Chemical Formulas 4.

[Chemical Formulas 4]

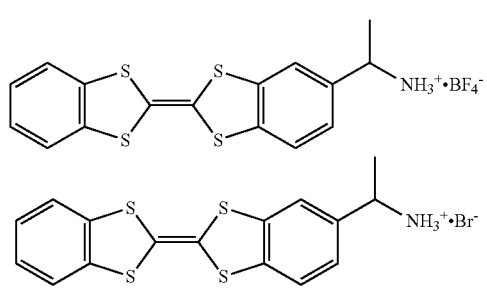

According to this configuration, there can be obtained an organic compound in which many functions are controllable.

A ninth aspect of the present invention lies in an organic compound characterized by being either one of the compounds expressed by the following Chemical Formulas 5.

[Chemical Formulas 5]

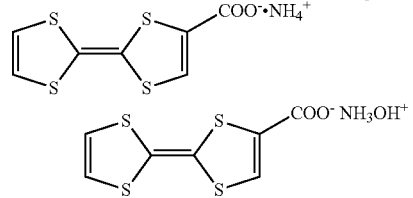

According to this configuration, there can be obtained an organic compound in which many functions are controllable.

A tenth aspect of the present invention lies in the organic compound according to any one of claim 4 to claim 9, characterized in that the compound is a semiconductor.

According to this configuration, there can be obtained a material in which many functions are controllable.

An eleventh aspect of the present invention lies in a semiconductor device, characterized by including the organic compound according to claim 10.

A twelfth aspect of the present invention lies in a solar cell, characterized by including the organic compound according to claim 10.

A thirteenth aspect of the present invention lies in an organic semiconductor compound, characterized by being a ammonium tetrathiafulvalene-2-carboxylic acid salt.

According to this configuration, there can be obtained an organic semiconductor compound which is chemically stable and which is hardly deteriorated.

A fourteenth aspect of the present invention lies in a producing method of an organic semiconductor compound, characterized in that an organic molecule which becomes a donor is formed by being salt-formed with an inorganic acid or an inorganic base by one to one and a self assembling compound is produced.

According to this configuration, there can be obtained an organic semiconductor compound by a simple technique.

A fifteenth aspect of the present invention lies in an organic semiconductor compound, characterized by having a quasi-closed-shell configuration.

According to this configuration, there can be obtained an organic semiconductor compound by a simple technique.

Here, with respect to the protic acid functional group, there exist, for example, —COOH, —SO$_3$H, —PO$_3$H, —PSO$_2$H. The first class amine is expressed, for example, by —NH$_n$D$_{3-n}$ (n=2 to 0) (here, D means deuterium). Also, with respect to the inorganic acid, there exist, for example, HBF$_4$, HClO$_4$, HCl, HBr, HI, DBF$_4$, DClO$_4$, DCl, DBr, DI. With respect to the inorganic base, there exist, for example, NH$_n$D$_{3-n}$ (n=3 to 0), NH$_n$D$_{2-n}$OH (n=2 to 0), NH$_n$D$_{2-n}$OD (n=2 to 0).

It should be noted that the wording semiconductor indicates, with respect to a conductor which conducts electricity and an insulator which does not conduct electricity, a material presenting property intermediate thereof. For example, it is a device whose electrical conductivity is in a range of approximately $10^2$ to $10^{-6}$ Scm$^{-1}$ (S is $\Omega^{-1}$) in the vicinity of the room temperature.

The wording donor indicates an electron donor (electron donor molecule or electron donor group). Also, the wording acceptor indicates an electron acceptor (electron acceptor molecule or electron acceptor group).

The wording "containing a tetrathiafulvalene affinity region in a framework" indicates a material having a tetrathiafulvalene structure in the framework of the molecule such as 1-(dibenzotetrathiafulvalene-2-yl)ethylamine, tetrathiafulvalene-2-carboxylic acid and the like.

Also, with respect to the compound described in the present specification and the present patent claims, a compound which has an equivalent structure and in which an element is substituted by an element isotope of deuterium or the like will be covered. Consequently, for example, in the Chemical Formulas 2 mentioned above, materials expressed by Chemical Formulas 2A mentioned below will be included.

[Chemical Formulas 2A]

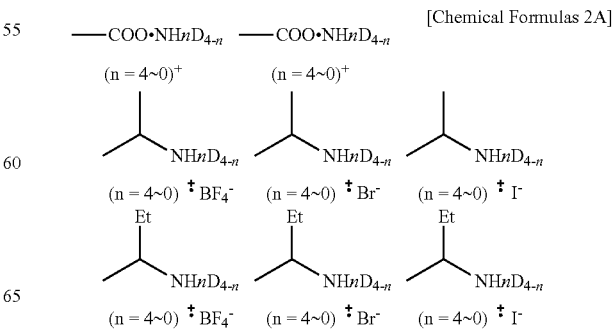

-continued

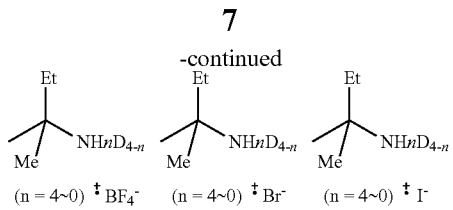

Effect of the Invention

According to the present invention, there can be obtained a compound or the like that can become a material in which many functions are controllable.

Still other objects, features or advantages of the present invention will become clear by the detailed description based on exemplified embodiments and attached drawings of the present invention, which will be described later.

BEST MODE FOR CARRYING OUT THE INVENTION

Figure 1:
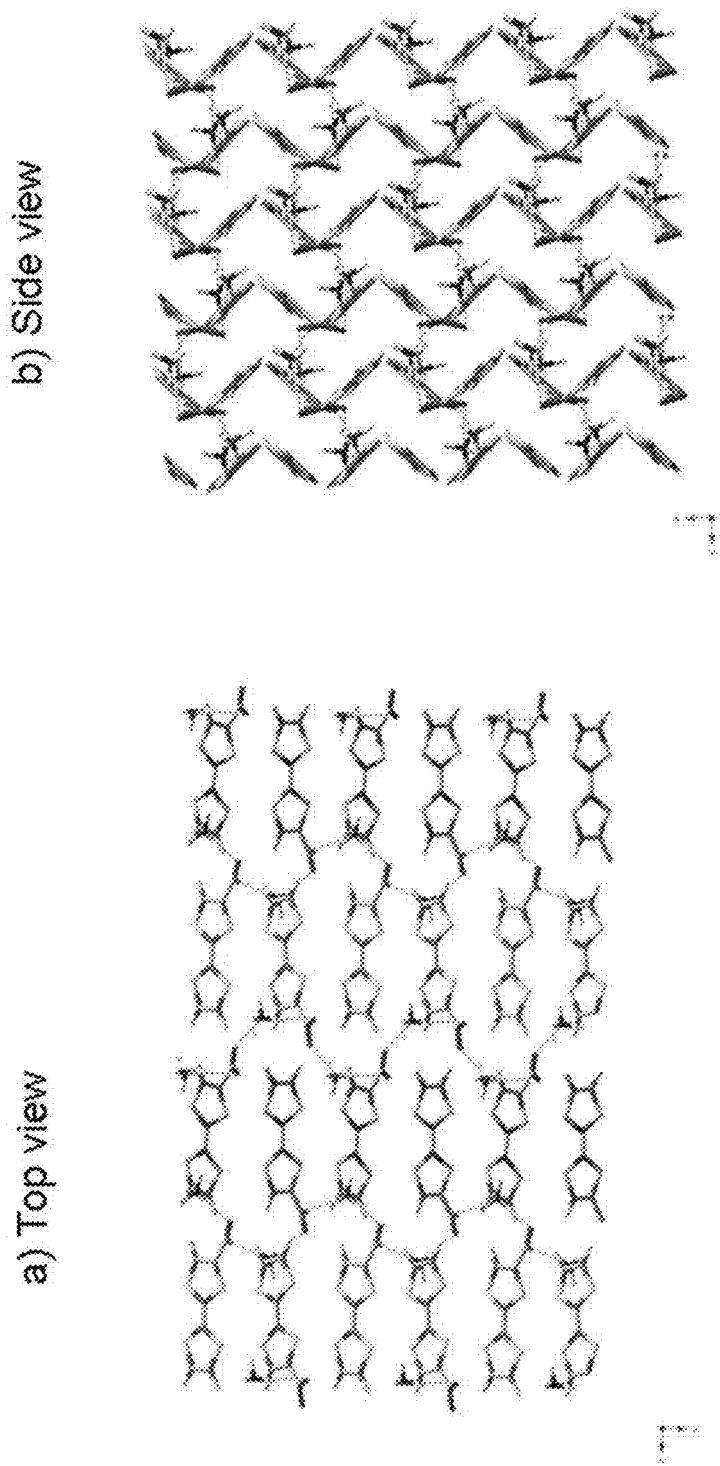
FIG. 1 is a schematic diagram showing a crystal structure at 300K.

Hereinafter, it will be explained with respect to exemplified embodiments of the present invention in detail while referring to drawings.

[Brief Summary]

As a result of day-to-day bona fide researches of the present inventors, it was proved that an organic semiconductor can be obtained by a simple technique such as to salt-form a donor molecule with an inorganic acid or an inorganic base. There is a prospect that a variety of organic semiconductors can be produced by similar techniques and this technique is an epoch-making technique. Here, two examples are briefly shown as illustrative embodiments thereof.

1) A tetrathiafulvalene-2-carboxylic acid was obtained by total yield 65% from tetrathiafulvalene (TTF) through two processes and thereafter, the salt was prepared by a 28% aqueous ammonia solution and a 1:1 ammonium tetrathiafulvalene-2-carboxylic acid salt which is pure at the element analysis level was obtained.

Electrical conductivity when pelletizing the obtained powder shaped solid was around $1.0 \times 10^{-3}$ S/cm at room temperature.

2) Ethyl methyl ketone was made to be a starting raw material, dibenzo tetrathiafulvalenyl ethylamine was obtained by total yield 1% through 15 processes and thereafter, the salt was prepared by a 42% tetrafluoroboric acid solution or by a 47-49% aqueous bromic acid solution and in both cases, a 1:1 dibenzo tetrathiafulvalenyl ethylamine-tetrafluoroboric acid salt and a dibenzo tetrathiafulvalenyl ethylamine-bromic acid salt which are pure at the element analysis level were obtained.

Electrical conductivity when pelletizing the obtained powder shaped amorphous solid was around $1.0 \times (10^{-3}$ to $10^{-4})$ S/cm at room temperature.

Next, it will be explained with respect to a brief summary or the like of a molecular association structure of an ammonium tetrathiafulvalene-2-carboxylic acid salt.

In a high temperature region of 200K or more, there was observed, in particular, a novel characteristic which did not exist up to now in an aspect that a high thermal electromotive force was generated depending on the mechanism derived from the rotating and vibrating motions of the ammonium region. From a fact that there is not exhibited so much excellent material property in case of substituting a counter cation which does not have hydrogen bonding capability with respect to the ammonium region and a portion of ammonium proton by a substituent group, it was proved experimentally that the rotating motion of the ammonium becomes a large key of the material property expression.

Also, with respect to the electrical conduction, it became clear from the frequency dependence of dielectric dispersion of the deuterated sample that the hydrogen bonding conspicuously have to do with the electron conduction.

The ammonium not only becomes a key of the material property expression but also assumes a role of self-assembling the TTF (donor) molecule effectively to a molecular arrangement suited for a carrier transport phenomenon.

First, as an example, it will be explained with respect to a crystal structure at 300K.

FIG. 1 is a schematic diagram showing a crystal structure at 300K. As shown in the drawing, a column shaped hydrogen bonding network is formed centering around ammonium and depending on the stacking thereof in a nested shape, effective π-π mutual interaction and S . . . S contact occur. It is possible for a carrier to move around in a two-dimensional arrangement.

Hereinafter, while illustrating by an example a specific compound, the material property or the like of the compound thereof will be explained in detail.

[Material Property or the Like]

First, it will be explained with respect to material property of a compound mentioned below.

[Chemical Formula 6]

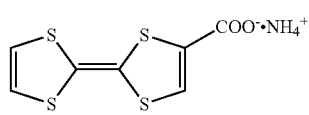

Figure 2:
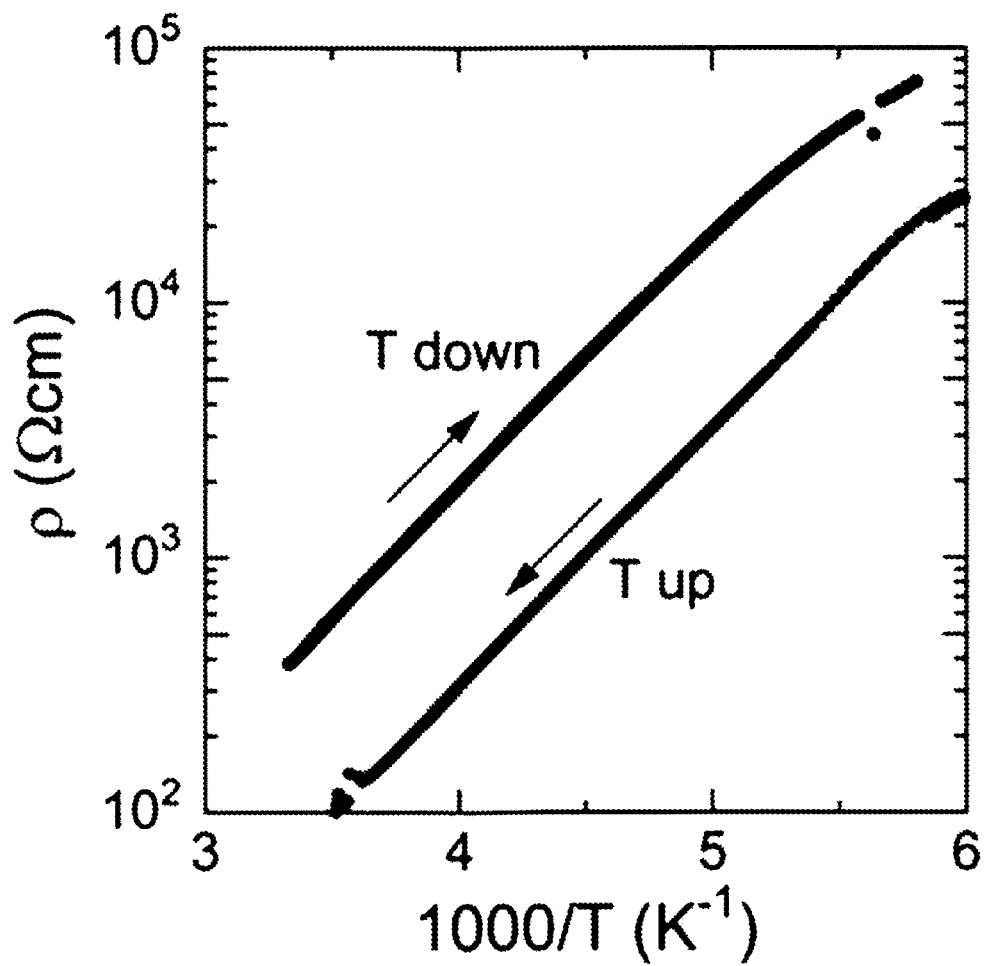
FIG. 2 is a diagram showing temperature dependence of electrical conductivity.
Figure 3:
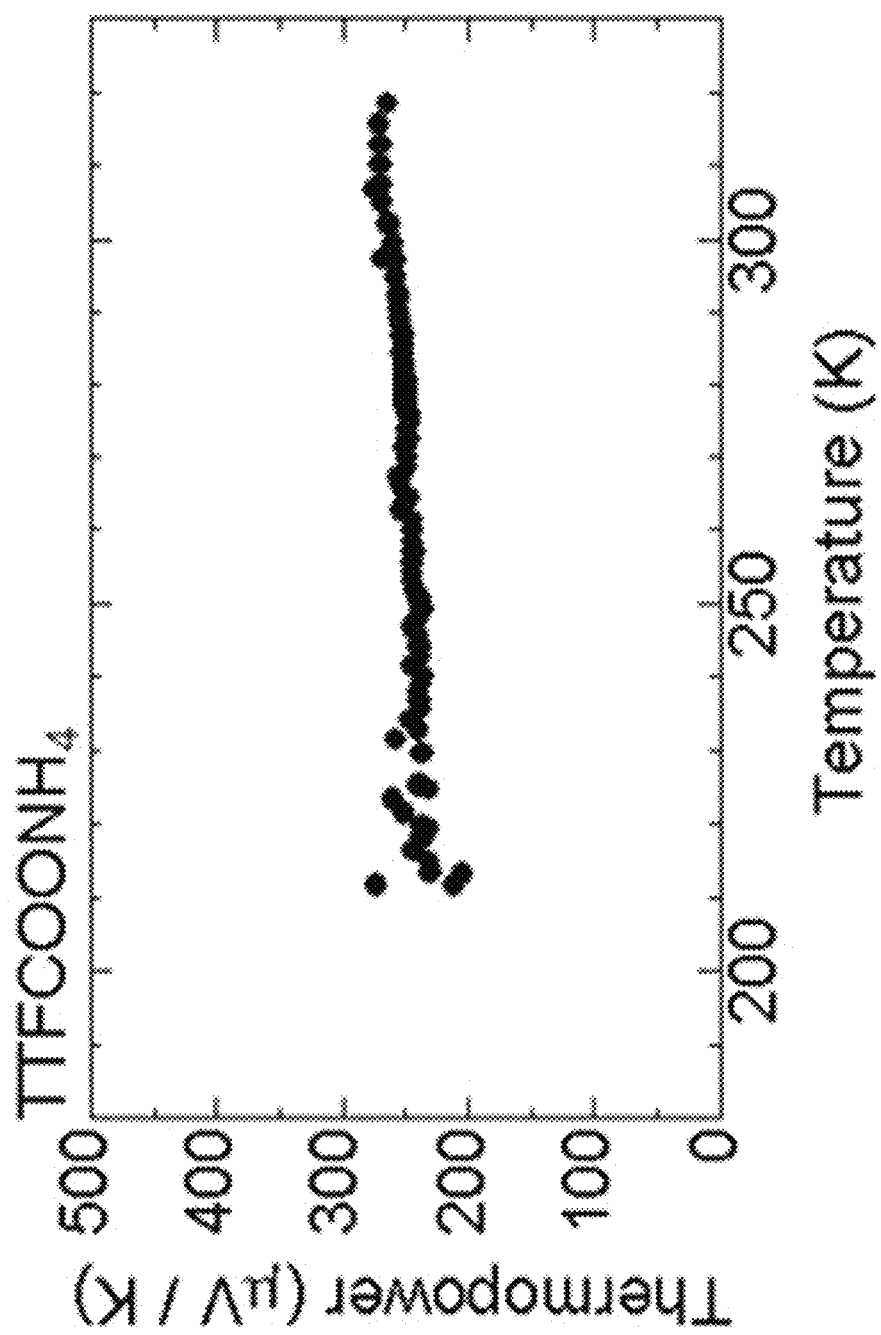
FIG. 3 is a diagram showing thermal electromotive force.

FIG. 2 is a diagram showing temperature dependence of electrical conductivity. On an occasion of measurement, a four-probe method was employed. FIG. 3 is a diagram showing thermal electromotive force. As shown in the drawing, even if changing the temperature from low temperature to high temperature or from high temperature to low temperature, there is not observed a change depending on phase transition and it is found out that the temperature dependence of electrical resistivity is that of a heat active type semiconductor. Also, it is found out that the temperature dependence of thermal electromotive force is very little and that this compound has an excellent material property in a wide temperature range. In particular, these data indicate a fact that there can be expected an application to a thermal power generation or the like which utilizes thermoelectric effect.

Figure 4:
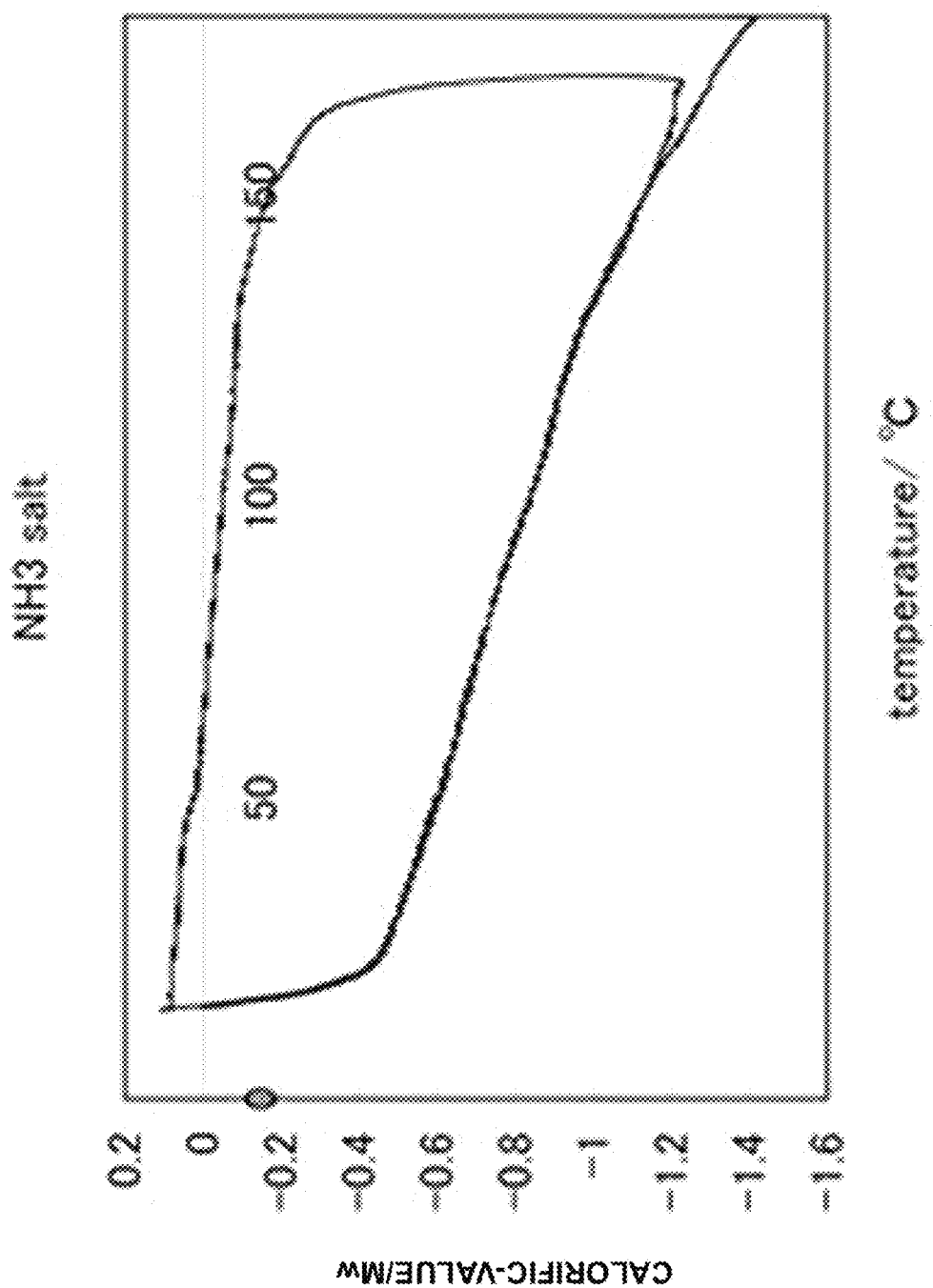
FIG. 4 is a diagram showing a calorific-value measurement result of a differential scanning calorimeter (DSC)
Figure 5:
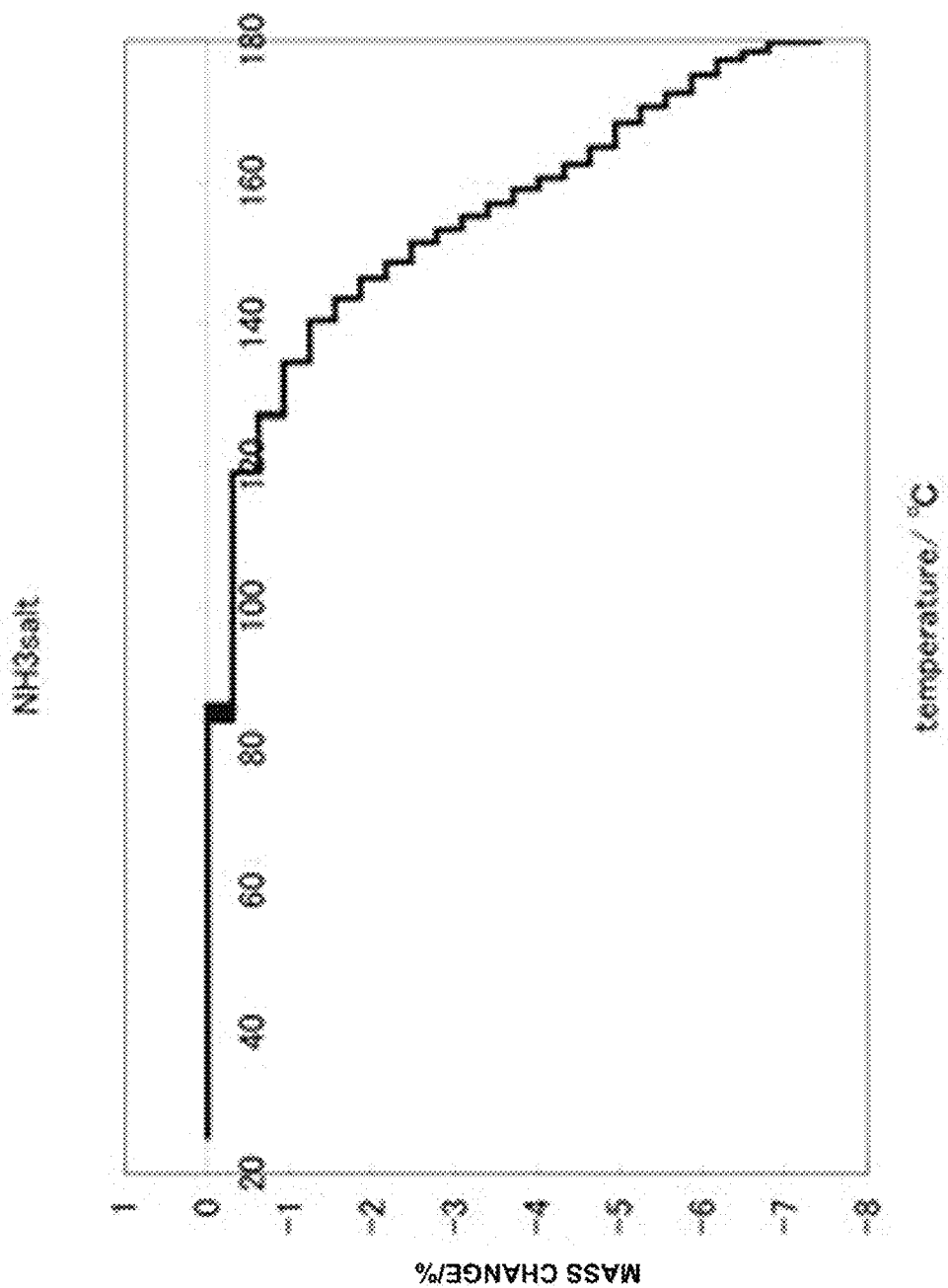
FIG. 5 is a diagram showing a thermogravimetric measurement result according to a thermogravimetric analyzer (TGA)

FIG. 4 is a diagram showing a calorific-value measurement result of a differential scanning calorimeter (DSC). FIG. 5 is a diagram showing a thermogravimetric measurement result according to a thermogravimetric analyzer (TGA). Any one of the measurement values is approximately stable until 140° C. or less, but when exceeding approximately 140° C., the measurement values changed largely. It is conceivable that this suggests that $NH_3$ is vanished when exceeding 140° C.

Figure 6:
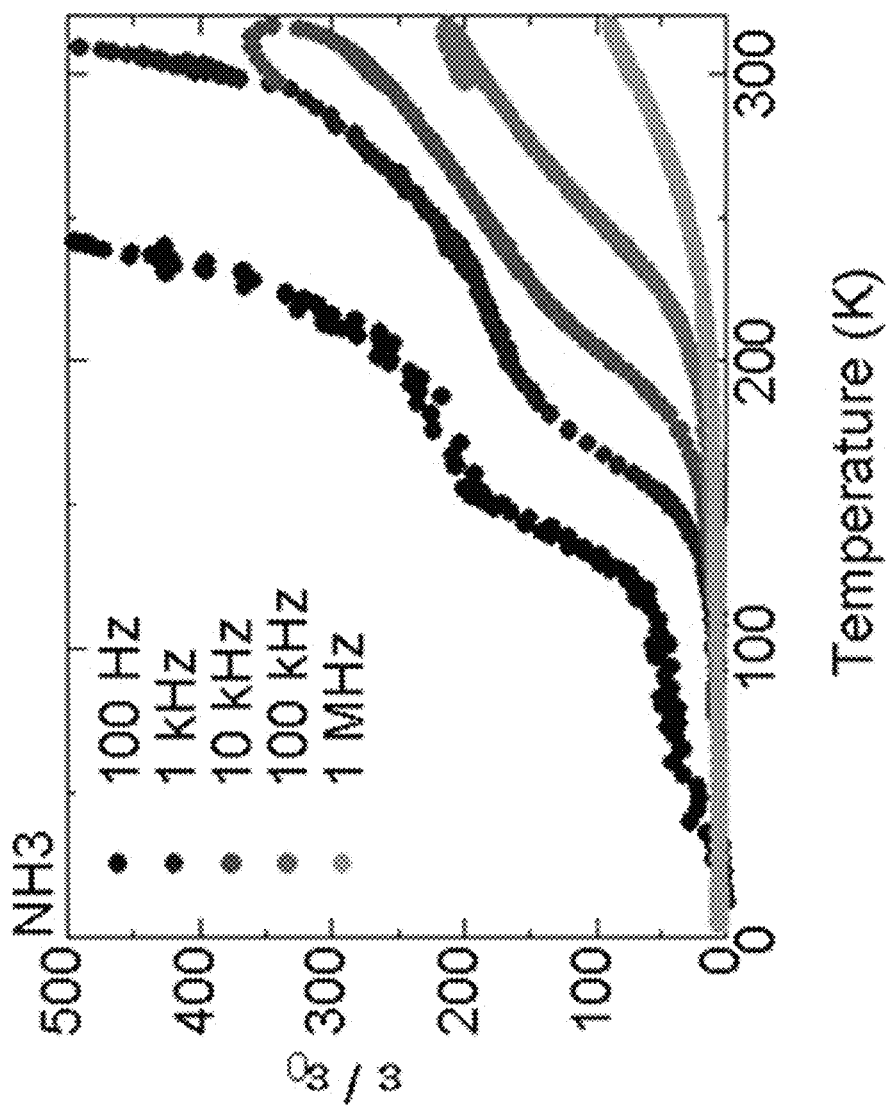
FIG. 6 is a diagram showing permittivity.

FIG. 6 is a diagram showing permittivity. As shown in the drawing, there were observed polarization and dielectric response. This result is to suggest possibility of an application as an actuator or the like which utilizes a ferroelectric memory and eventually a piezoelectric effect depending on the ferroelectricity.

Figure 7:
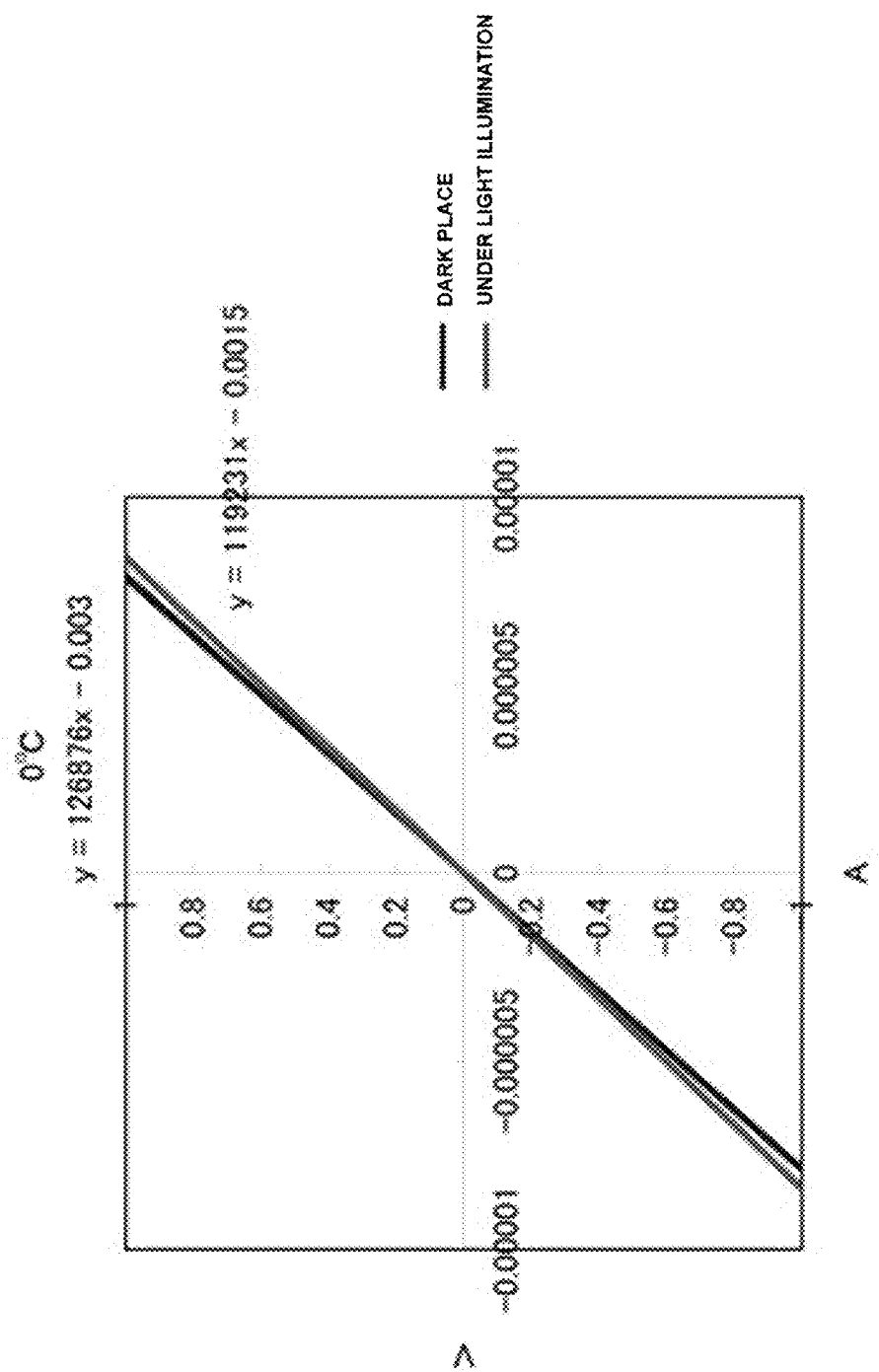
FIG. 7 is a diagram showing measured data when measuring photoconductivity while changing temperature.
Figure 8:
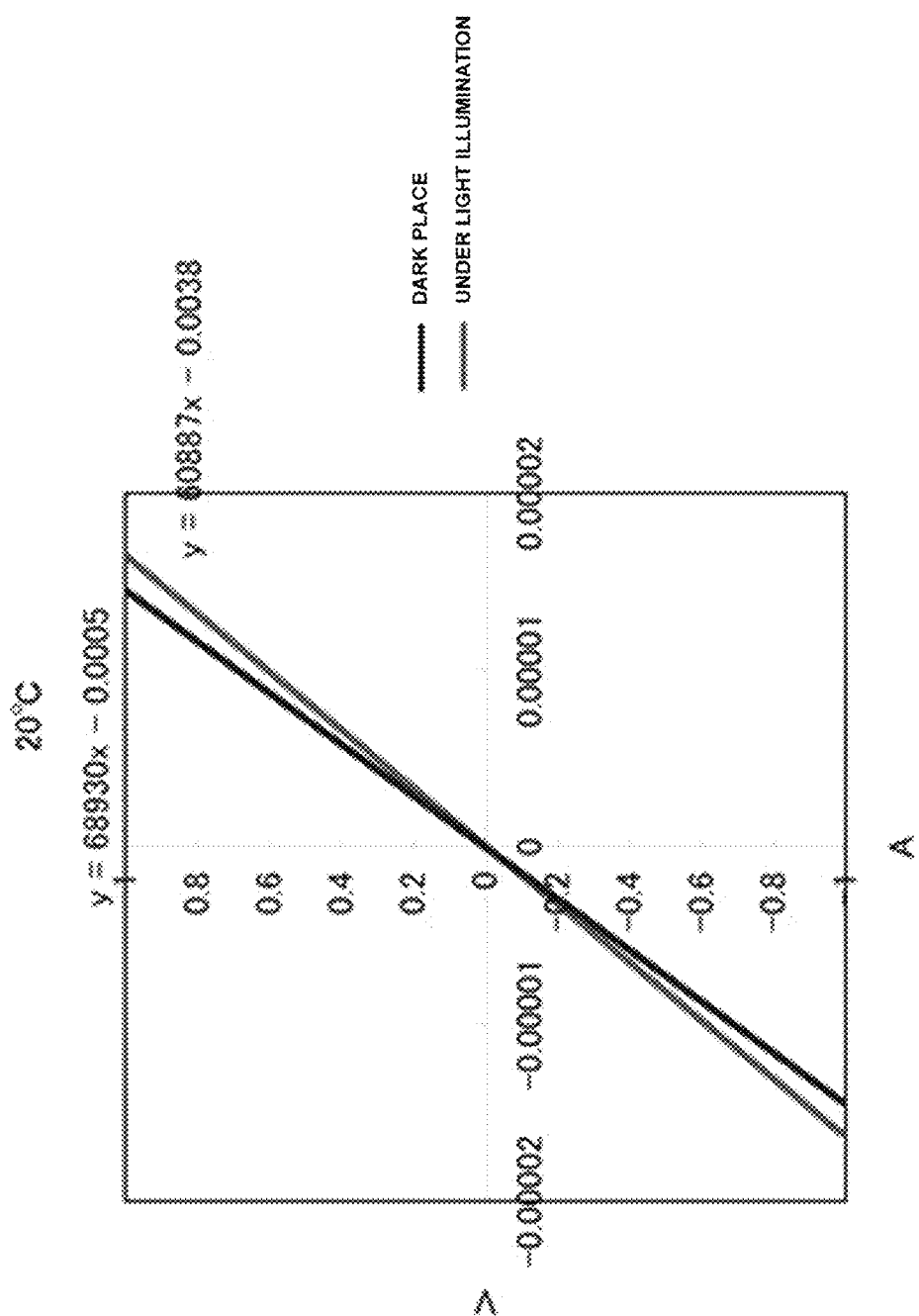
FIG. 8 is a diagram showing measured data when measuring photoconductivity while changing temperature.
Figure 9:
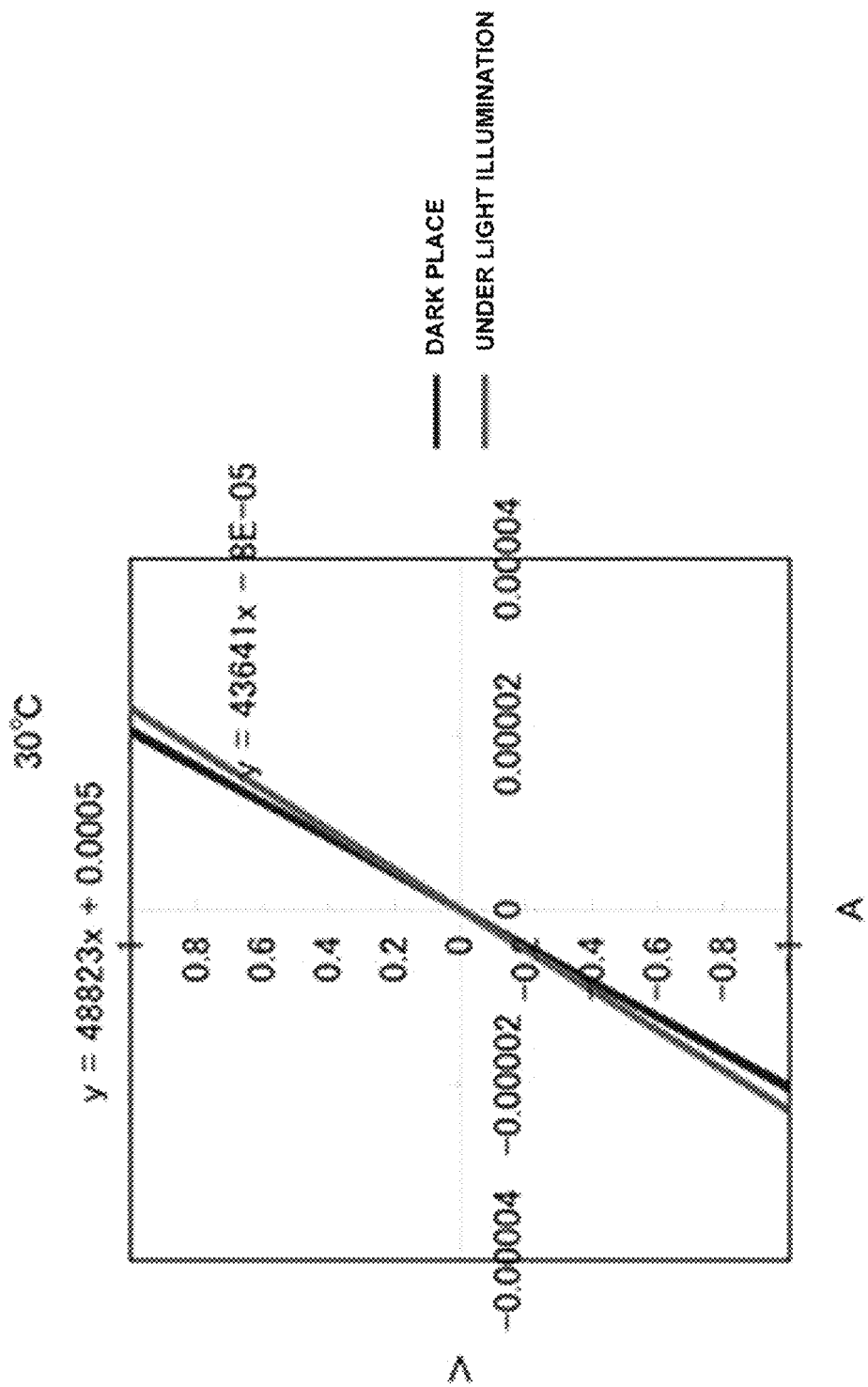
FIG. 9 is a diagram showing measured data when measuring photoconductivity while changing temperature.

FIG. 7, FIG. 8 and FIG. 9 are diagrams showing measured data when measuring photoconductivity while changing temperature. FIG. 7, FIG. 8 and FIG. 9 indicate data when the measurements were carried out at 0° C., 20° C., 30° C. respectively. A pelletized sample (width: 0.08 cm, thickness: 0.03 cm) was used and there was employed a two-terminal method in which terminal attachment is performed by using a silver paste. Also, there was executed a light illumination of a wavelength region which includes all of the visible light region.

Next, it will be explained with respect to the material property of a compound mentioned below.

[Chemical Formula 7]

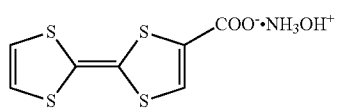

Figure 10:
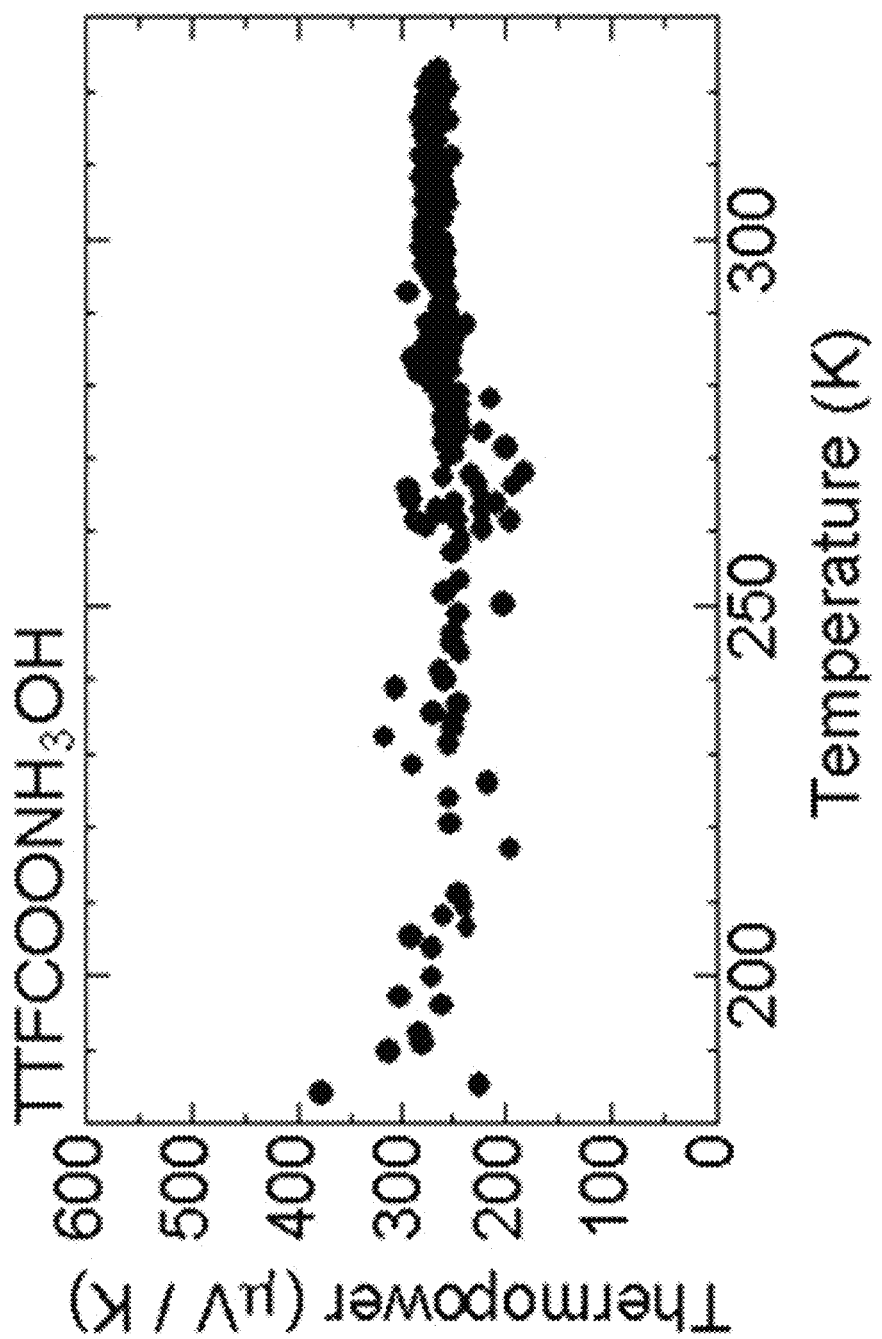
FIG. 10 is a diagram showing thermal electromotive force.

FIG. 10 is a diagram showing thermal electromotive force. Similarly as the compound mentioned above, even if changing the temperature from low temperature to high temperature or from high temperature to low temperature, there is not observed a change depending on the phase transition and it is found out that the temperature dependence of electrical resistivity is that of a heat active type semiconductor. Also, it is found out that the temperature dependence of thermal electromotive force is very little and that also this compound has an excellent material property in a wide temperature range. These data indicate a fact that there can be expected an application to a thermal power generation or the like which utilizes thermoelectric effect also with respect to this compound.

Next, it will be explained with respect to the material property of a compound mentioned below.

[Chemical Formula 8]

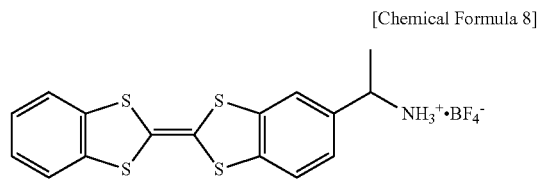

Figure 11:
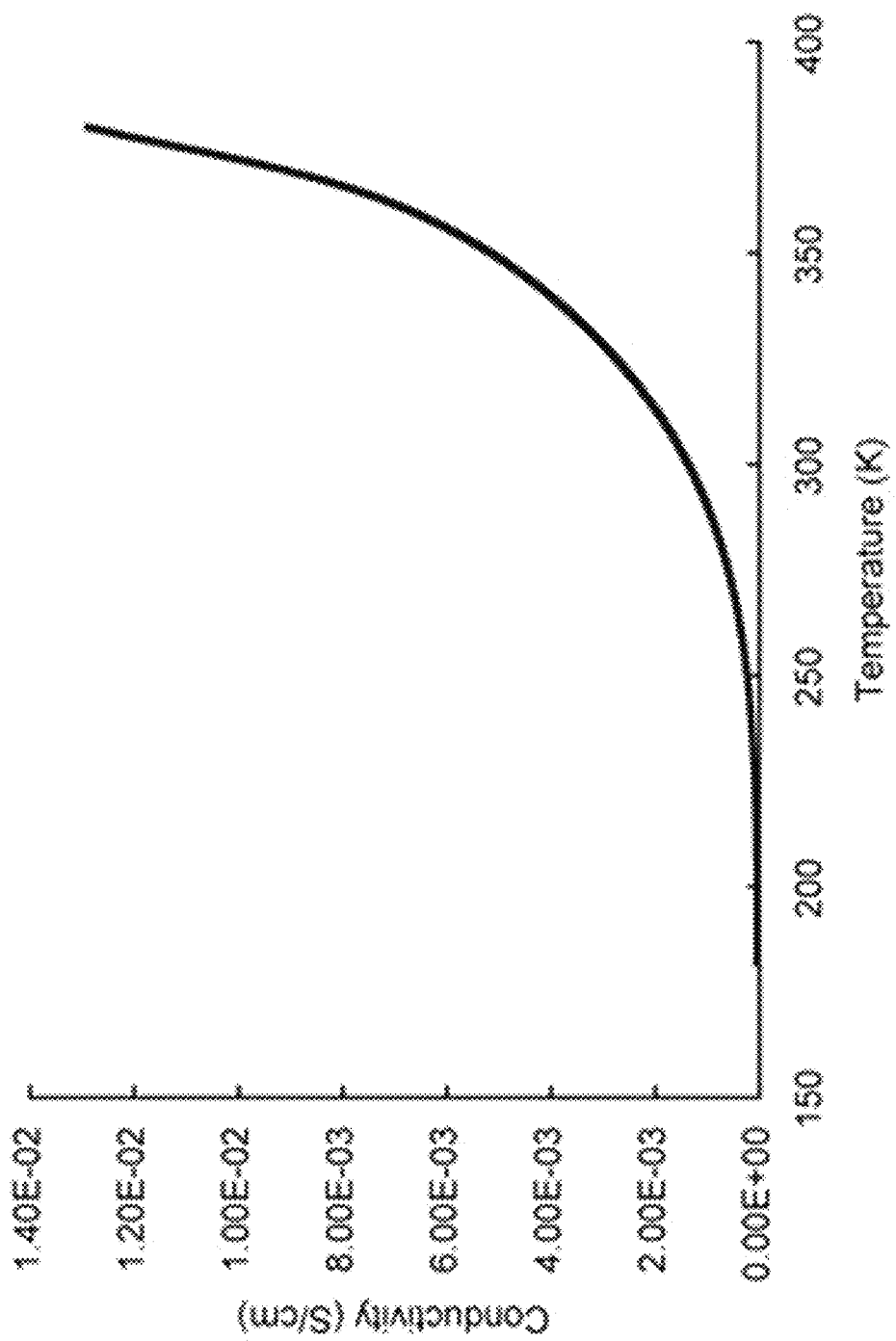
FIG. 11 is a diagram showing temperature dependence of electrical conductivity.
Figure 12:
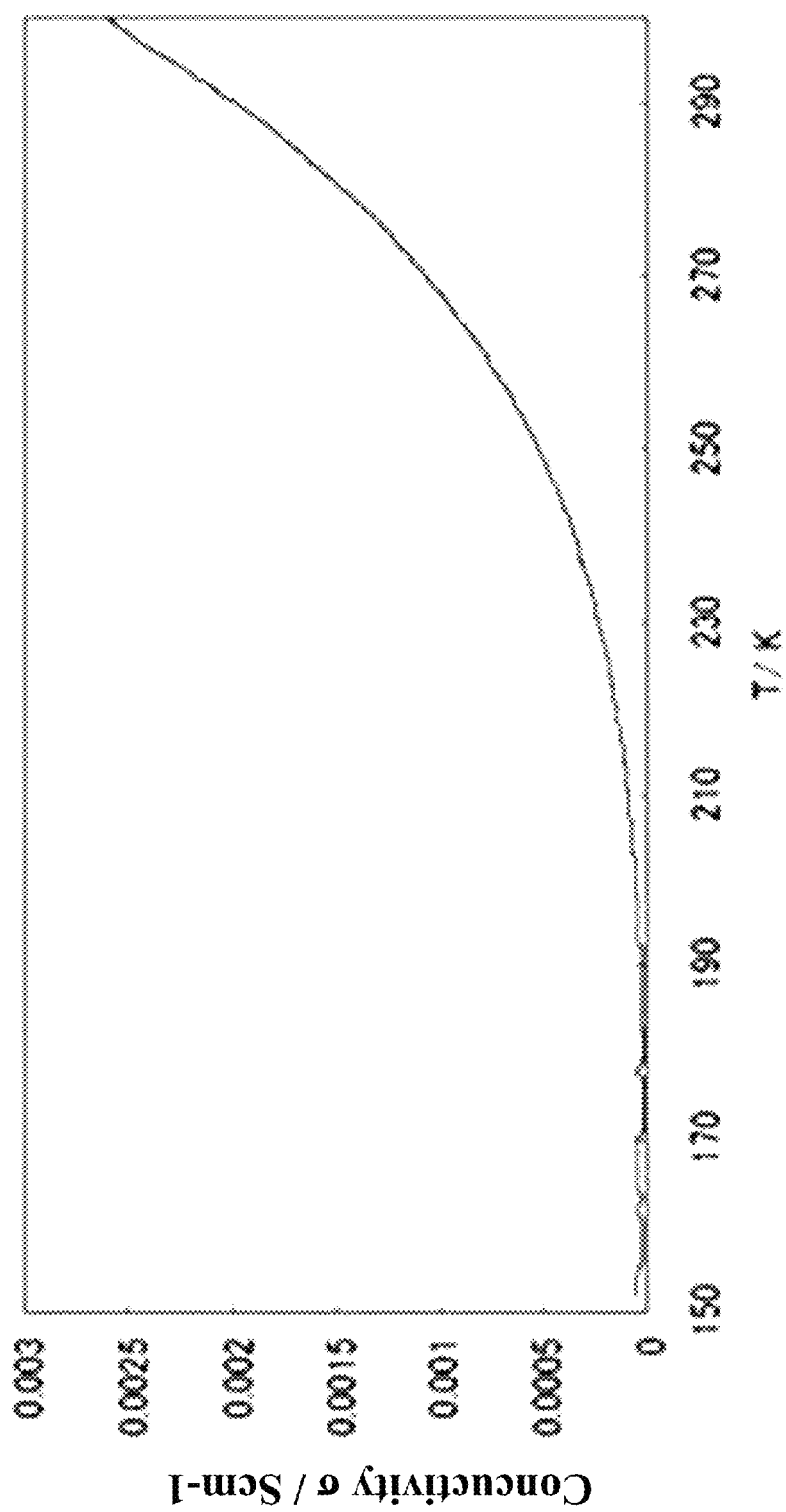
FIG. 12 is a diagram showing temperature dependence of electrical conductivity.

FIG. 11 is a diagram showing temperature dependence of electrical conductivity. On the other hand, FIG. 12 is a diagram showing temperature dependence of electrical conductivity of a compound expressed by Chemical Formula 6. As shown in the drawing, the temperature dependences of electrical conductivity of both the sides are very similar and it will be suggested that like material properties will be presented also for other aspects.

[Chemical Formula 9]

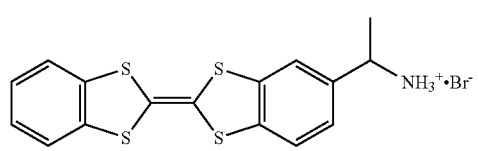

Figure 13:
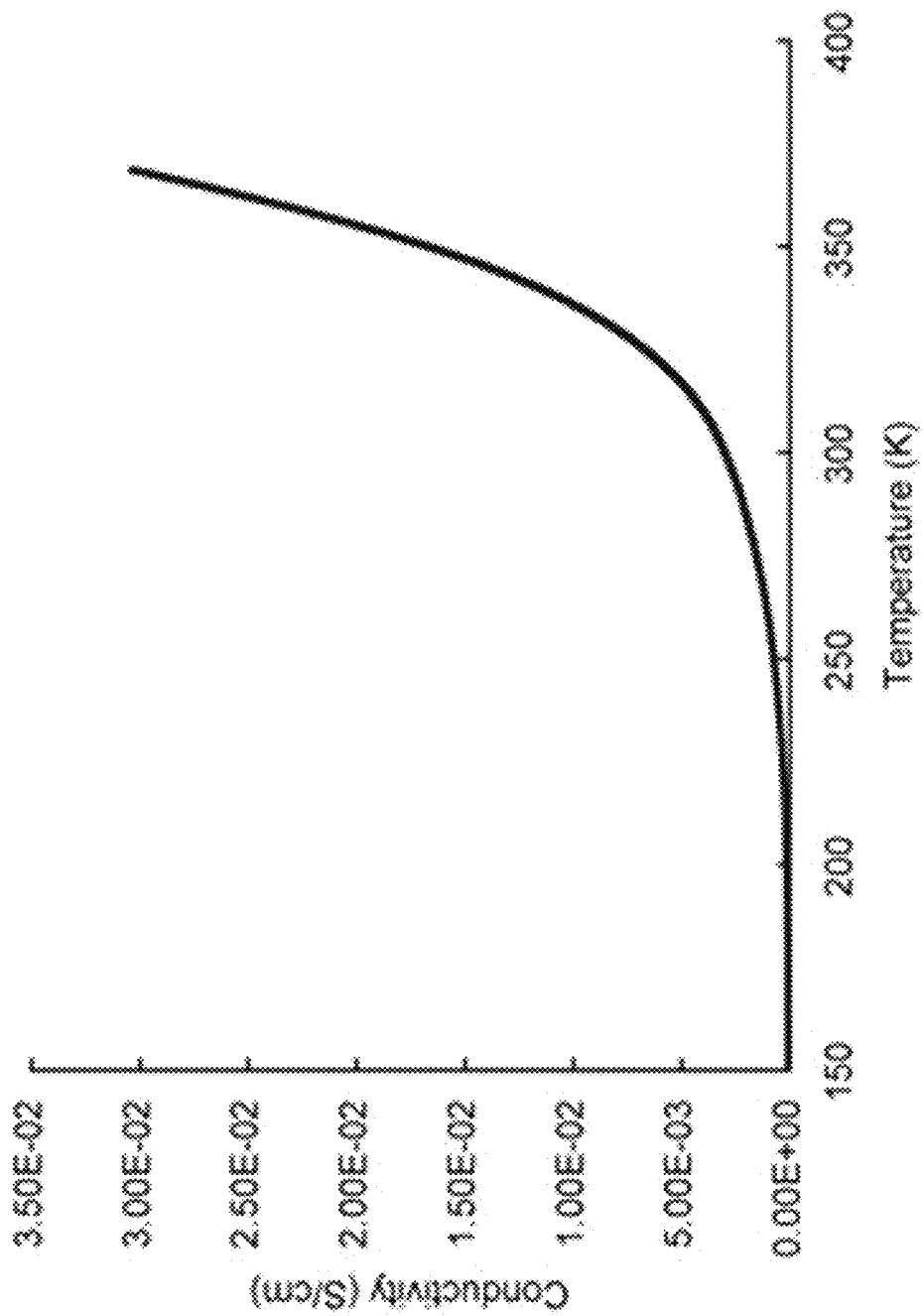
FIG. 13 is a diagram showing a diffuse reflectance spectrum.

FIG. 13 is a diagram showing temperature dependence of electrical conductivity. On the other hand, FIG. 12 is a diagram showing temperature dependence of electrical conductivity of a compound expressed by Chemical Formula 6. As shown in the drawings, the temperature dependences of electrical conductivity of both the sides are very similar and it will be suggested that like material properties will be presented also for other aspects.

Figure 14:
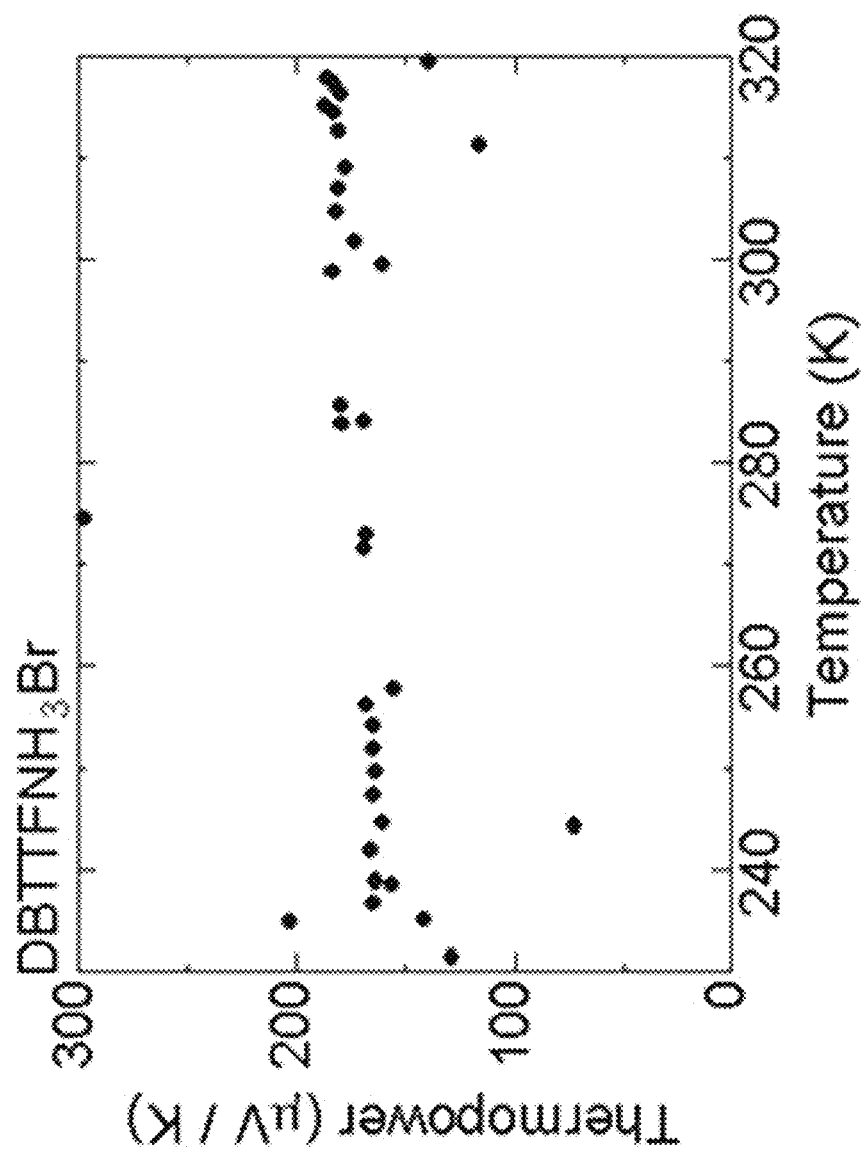
FIG. 14 is a diagram showing temperature dependence of thermal electromotive force.

FIG. 14 is a diagram showing temperature dependence of thermal electromotive force. From a fact that high thermal electromotive force is presented similarly as FIG. 3 and FIG. 10 and concurrently, temperature dependence is little, it is found out that also this compound has an excellent material property. These data indicate a fact that there can be expected an application to a thermal power generation or the like which utilizes thermoelectric effect also with respect to this compound.

Figure 15:
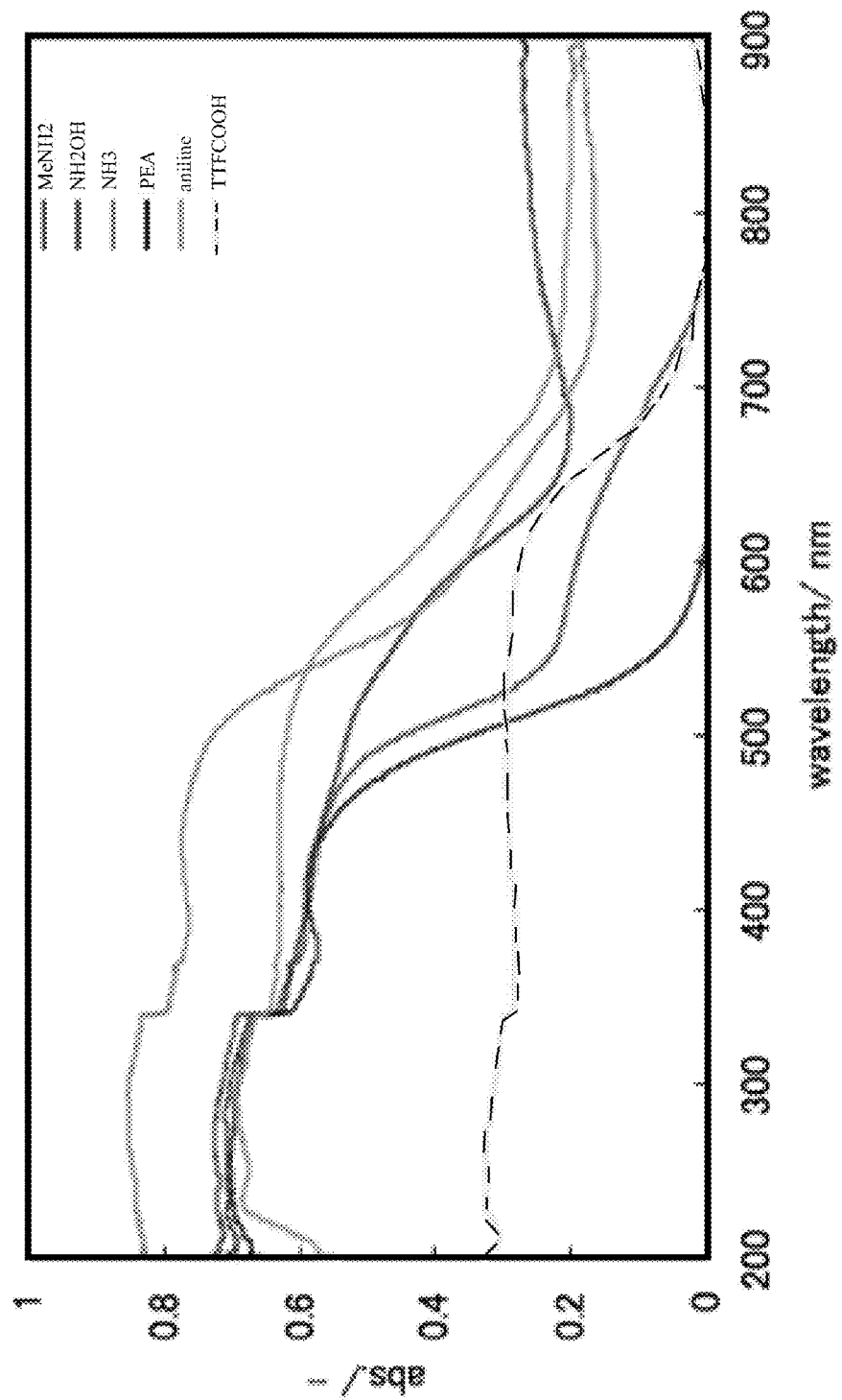
FIG. 15 is a diagram showing diffuse reflectance spectra of respective compounds.

FIG. 15 is a diagram showing diffuse reflectance spectra of respective compounds. As shown in the drawing, it was proved that respective compounds are different from usual acid-base salts and have absorption until the vicinity of 900 nm. This shows a fact that absorption of electromagnetic waves of long wavelengths is realized and that these compounds are suitable for the application to solar cells or the like.

It should be noted that compounds mentioned below are classified into two groups from a viewpoint of electrical conductivity.

1) Group in which Electrical Conductivity is around $10^{-2}$ S/cm

[Chemical Formulas 10]

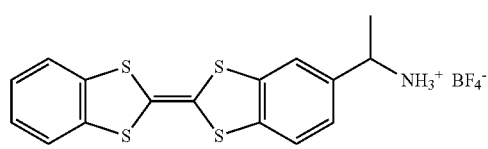

1-(dibenzotetrathiafulvalene-2-yl) Ethylamine-Boron Tetrafluoride Salt

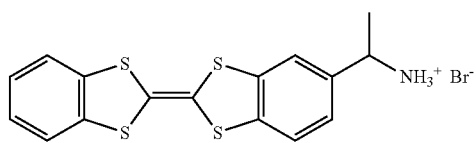

1-(dibenzotetrathiafulvalene-2-yl) Ethylamine-Bromic Acid Salt

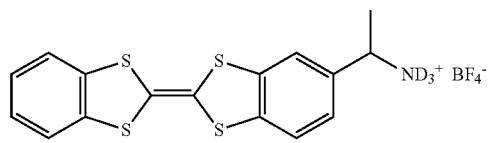

deuterated 1-(dibenzotetrathiafulvalene-2-yl) Ethylamine-Boron Tetrafluoride Salt

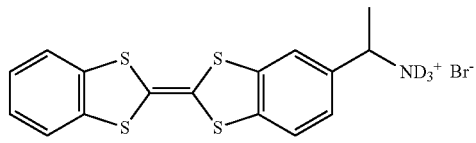

deuterated 1-(dibenzotetrathiafulvalene-2-yl) Ethylamine-Bromic Acid Salt

2) Group in which Electrical Conductivity is around $10^{-3}$ S/cm

[Chemical Formulas 11]

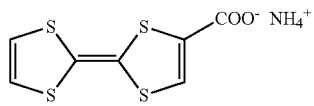

ammonium tetrathiafulvalene-2-carboxylic acid salt

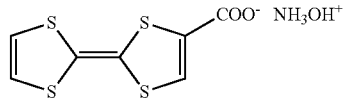

hydroxyammonium tetrathiafulvalene-2-carboxylic acid salt

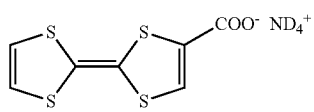

deuterated ammonium tetrathiafulvalene-2-carboxylic acid salt

-continued

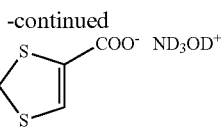

deuterated hydroxyammonium tetrathiafulvalene-2-carboxylic acid salt

[Molecular Association Structure]

Figure 16:
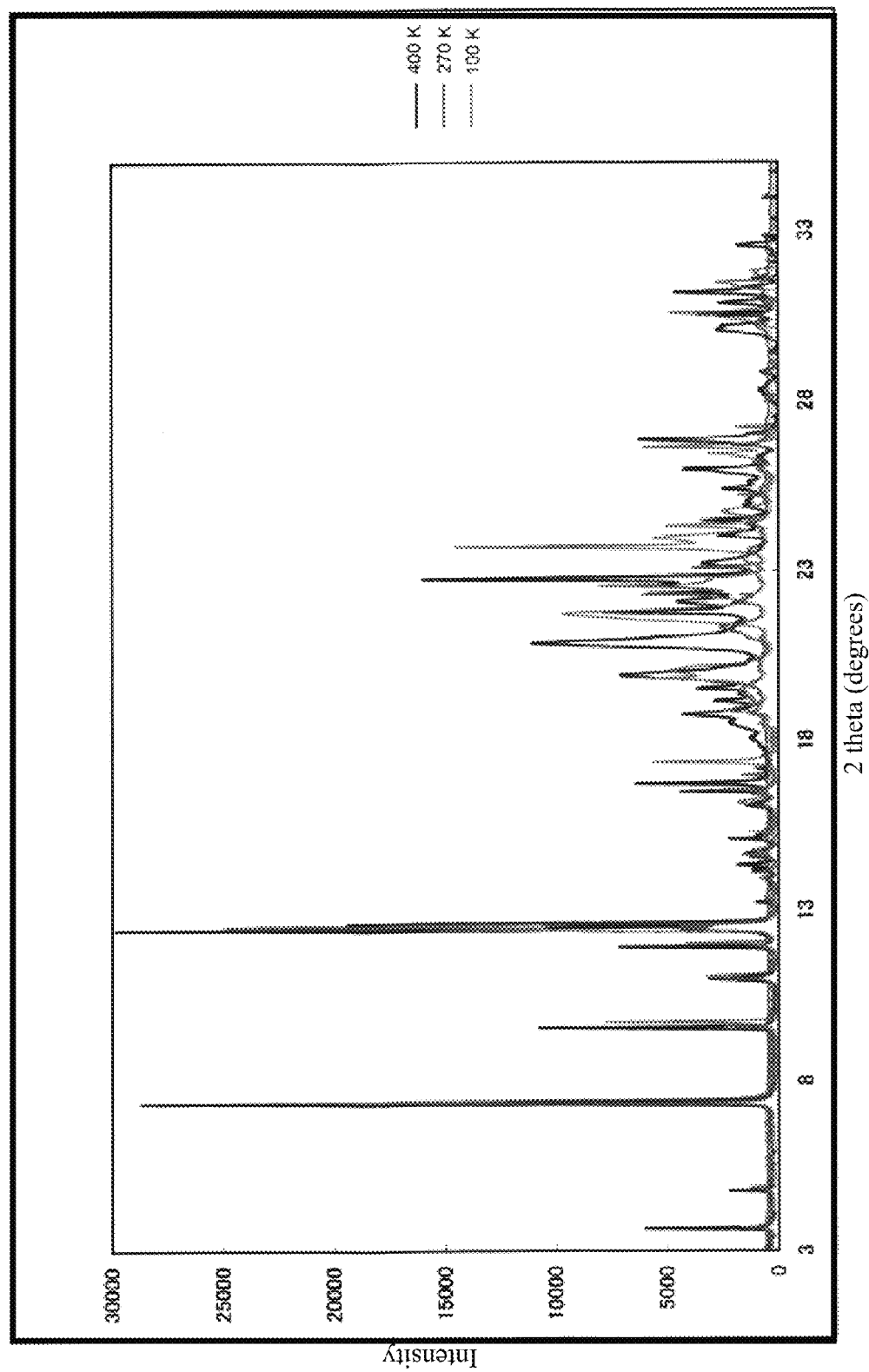
FIG. 16 is an X-ray crystal structure analysis of the powder of an ammonium tetrathiafulvalene-2-carboxylic acid salt.
Figure 17:
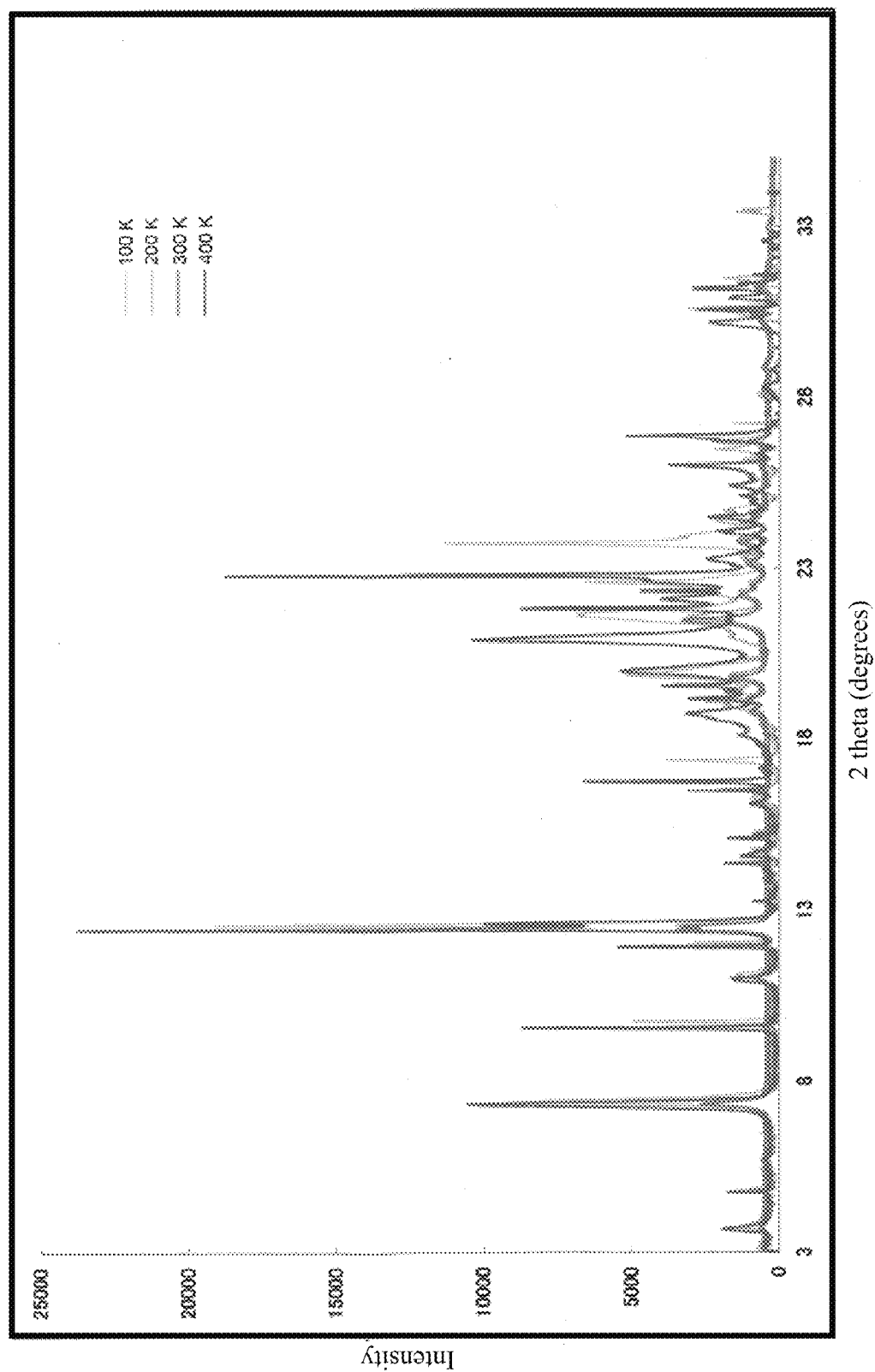
FIG. 17 is an X-ray crystal structure analysis of the powder of a deuterated ammonium tetrathiafulvalene-2-carboxylic acid salt.

FIG. 16 is an X-ray crystal structure analysis of the powder of an ammonium tetrathiafulvalene-2-carboxylic acid salt. Also, FIG. 17 is an X-ray crystal structure analysis of the powder of a deuterated ammonium tetrathiafulvalene-2-carboxylic acid salt. In both cases, a synchrotron light was used and the measurement was carried out under a condition of 1.3000 angstrom thereof. It is clear, by analyzing those above, that the ammonium tetrathiafulvalene-2-carboxylic acid salt becomes in a microcrystalline state having constant regularity in the molecular association structure thereof.

Figure 18:
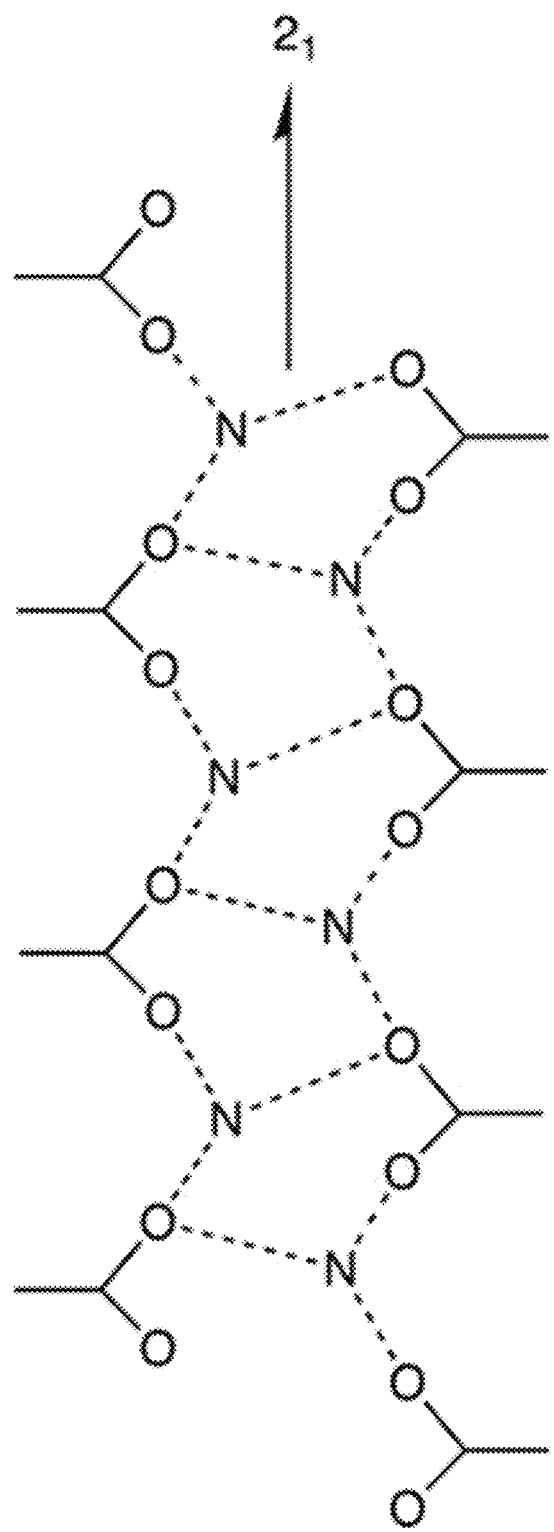
FIG. 18 is a schematic diagram showing a three dimensional structure when focusing attention on an intermolecular bonding and an intermolecular interaction.
Figure 19:
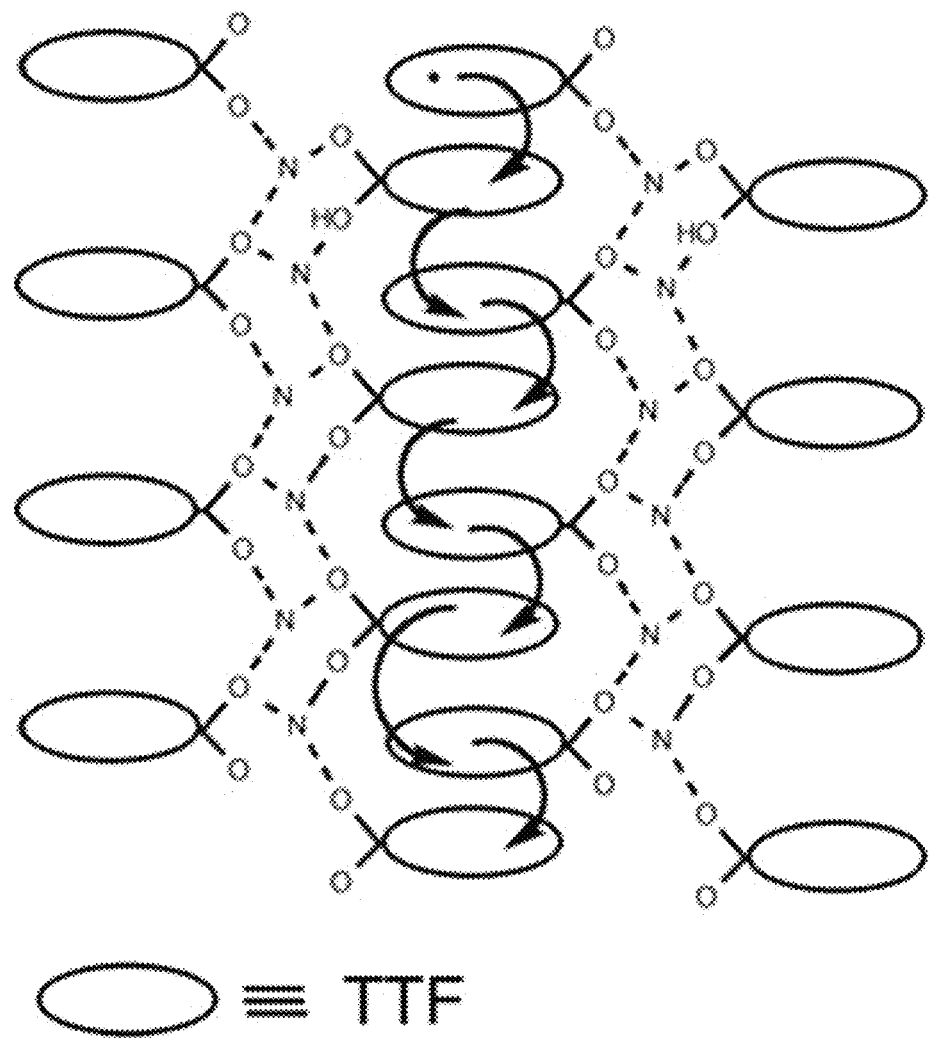
FIG. 19 is a schematic diagram showing a three dimensional structure when focusing attention on an intermolecular bonding and an intermolecular interaction.

FIG. 18 and FIG. 19 are schematic diagrams showing three dimensional structures when focusing attention on intermolecular bonding and intermolecular interaction. As shown in the drawings, respective molecules overlap in a compound of an ammonium tetrathiafulvalene-2-carboxylic acid salt or the like, there exist, among the molecules, a lot of loose bondings by hydrogen bondings and, as a whole, TTF regions are arranged in a column shape. Contact distance of an S atom and an S atom is 3.5 angstrom or less, orbitals of the neighboring S atoms overlap and a stable three dimensional structure is maintained.

[Quasi-Closed-Shell Configuration]

A quasi-closed-shell configuration is realized by a simple technique such that an organic radical species is buried into a closed-shell molecular arrangement by self assembly depending on a hydrogen bonding network composed of acid and base, which becomes a key of carrier generation. The wording "quasi-closed-shell configuration" means an electron configuration which can be seen, for example, on d orbital of transition metal and particularly on f orbital of rare earth metal, and in this configuration, spin does not play a role in chemical bonding, a low orbital energy is possessed and it is shielded by other electrons in a high energy state, so that isolation and localization occur inside the atomic orbital. This attracts a strong electron correlation effect in a solid state and becomes a source of various sorts of high material-property expressions which are specific for strongly correlated system metals. Also, this system is referred to as "heavy electron system", because the effective mass of the electron is made to increase derived from the strong electron correlation effect. A series of compound groups which have been explained until now are classified as f electron system metals which were realized for the first time in the field of the organic solid.

This fact is confirmed depending on a theoretical calculation. Based on atomic coordinates of a TTFCOO—NH$_4$ salt which was obtained from a powder X-ray crystal structure, ab initio calculation (quantum chemical calculation) was carried out by using a cluster model in which one piece of organic radical species was buried in a number of atoms between 2 pieces or more and 60 pieces or less by hydrogen bonding.

Figure 20:
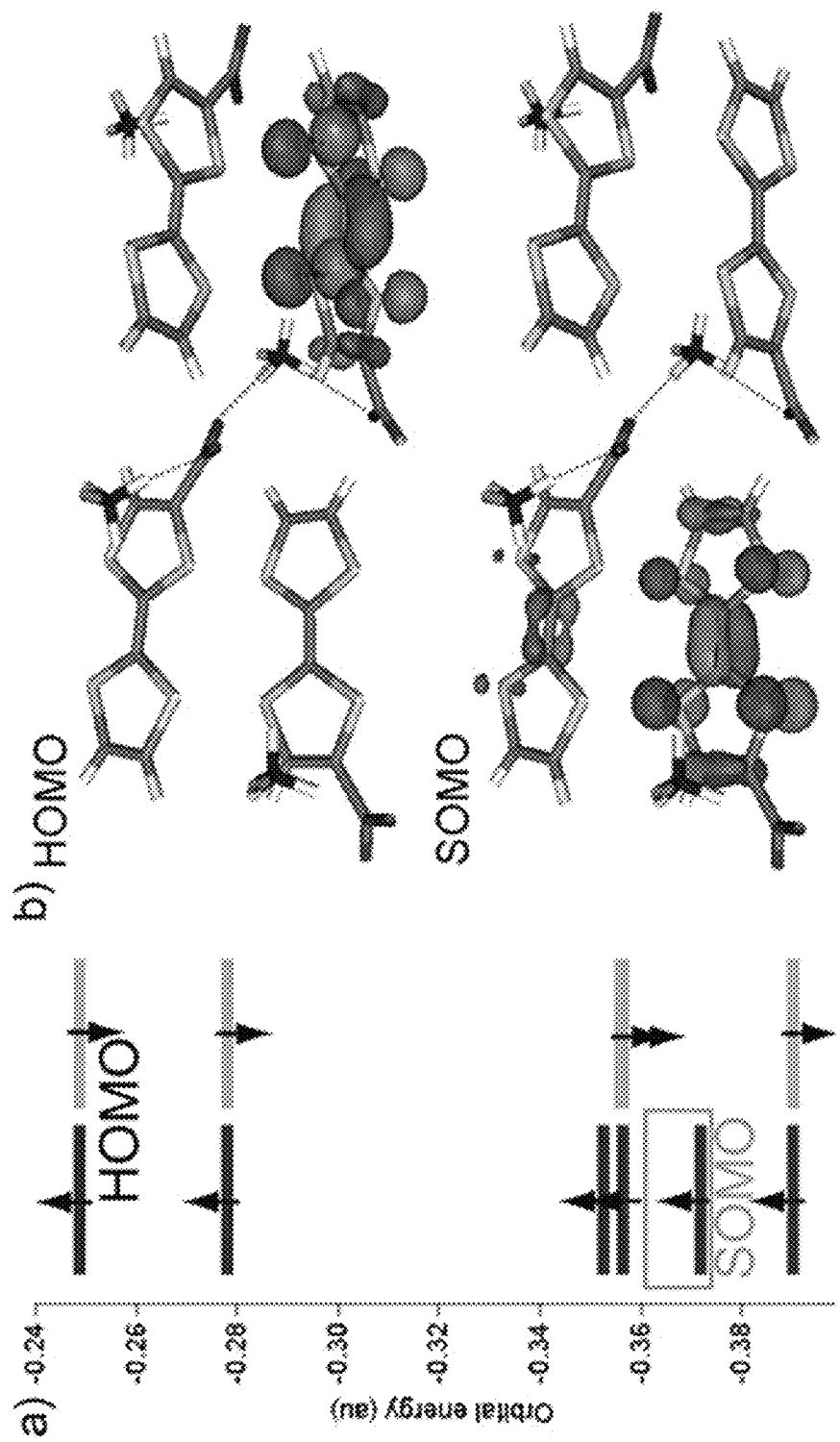
FIG. 20 is a diagram showing an electronic state by Unrestricted Hartree-Fock Method (UHF)/6-31G* using a model in which one-molecule of radical species TTF$^{·+}$COO—NH$_4$ is buried in the tetramer of a TTFCOO—NH$_4$ salt.

FIG. 20 is a diagram showing an electronic state by Unrestricted Hartree-Fock Method (UHF)/6-31G* using a model in which one-molecule of radical species TTF$^{+}$COO—NH$_4$ is buried in the tetramer of a TTFCOO—NH$_4$ salt. In the drawing, there are presented a) Quasi-Closed-Shell Configuration and b) Molecular Orbital Diagram. In each of the results, it became clear that singly occupied molecular orbital (SOMO) of the radical species does not exist on the frontier orbital and exists by being localized on an orbital which is more stabilized. This quasi-closed-shell configuration appears with respect to a compound having a shape in which a radical species is buried in an ultra molecular arrangement utilizing hydrogen bonding.

As an example, there are enumerated, hereinafter, acceptor molecules which are considered to express similar effects in the acceptor molecules.

[Chemical Formulas 12]

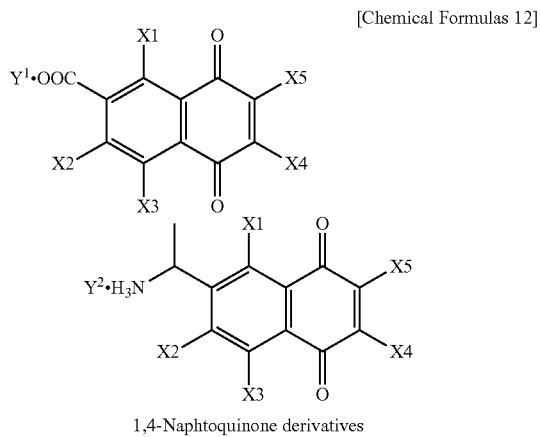

Figure 21:
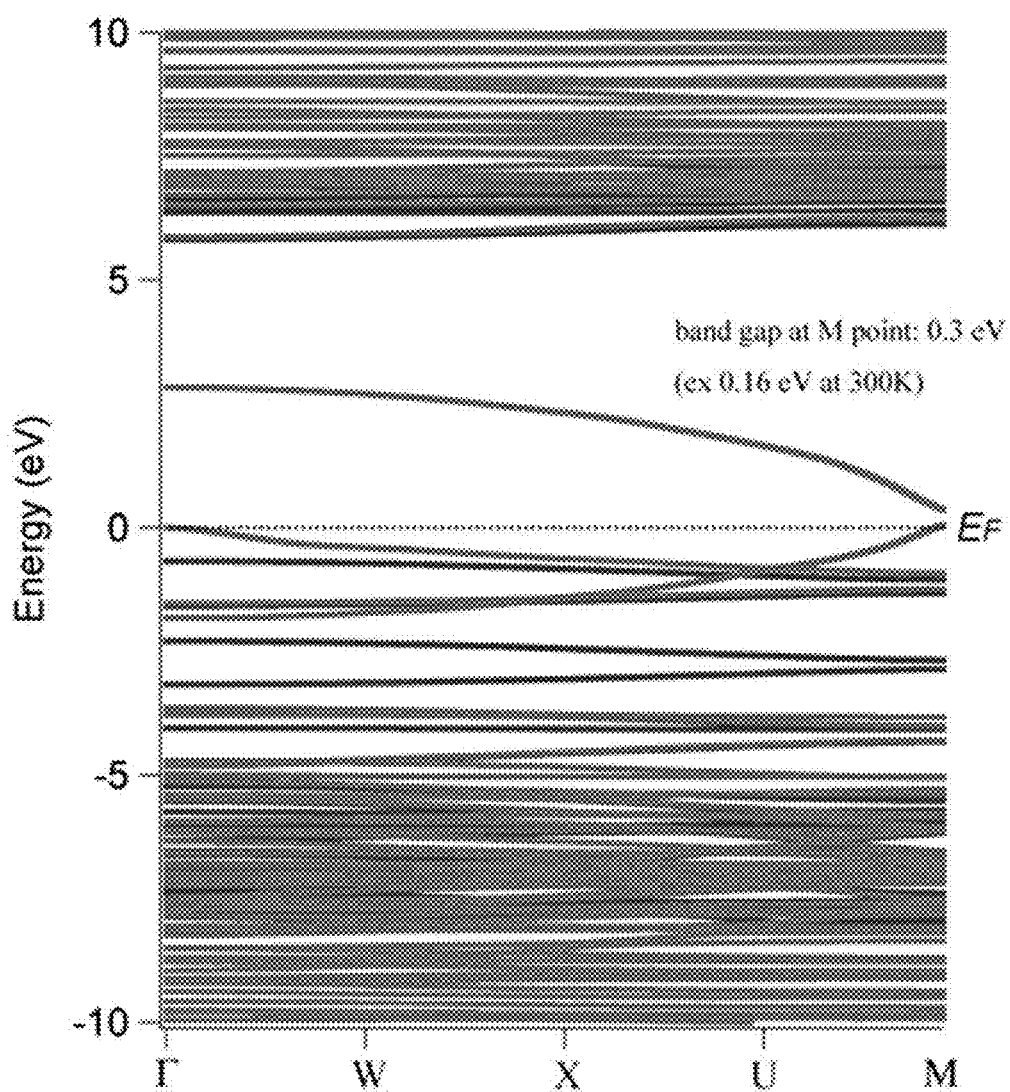
FIG. 21 is a diagram showing a result of periodic quantum chemical calculation which was carried out by considering the periodicity of hydrogen bonding direction (one-dimensional) with respect to a cluster model containing one radical species in four molecular unit.

1,4-Naphtoquinone derivatives $X_1, X_2, X_3, X_4, X_5 = H, D, NO_2, CN, F, Cl, Br, I$
$Y^1 = NH_4, ND_4, NH_3OH, ND_3OD$
$Y^2 = BF_4, F, Cl, Br, I, SO_3H$ FIG. 21 is a diagram showing a result of periodic quantum chemical calculation which was carried out by considering the periodicity of hydrogen bonding direction (one-dimensional) with respect to a cluster model containing one radical species in four molecular unit. A band gap of an M point is mere 0.3 eV and semiconductor-like properties are well reproduced. This confirms that conduction carriers are generated based on a fact that the orbital in the vicinity of SOMO is split depending on the quasi-closed-shell configuration. It should be noted that the calculation method was just as follows.

Periodic Boundary Condition (PBC)-UHF/3-21G*
Brillouin zone sampling: 40 k×1×1 points
Calculation program: Gaussian03, Rev. D 01
[Synthesis Method]

Next, it will be explained with respect to specific synthesis methods of the compounds.

Synthesis of Tetrathiafulvalene-2-carboxylic Acid

Absolute diethylether (10 ml) was added into diisopropylamine (0.65 ml, 5.42 mmol) under an argon atmosphere and n-BuLi (1.65 mol/L, 5.45 mmol) was slowly dropped thereto. This was stirred on an ice bath for one hour and lithiumdiisopropylamide (LDA) was prepared. Tetrathiafulvalene (TTF) (1.014 g, 4.96 mmol) was dissolved into absolute diethylether (100 ml) under an argon atmosphere and while stirring it at −78° C., the prepared LDA was slowly dropped thereto by using a canular. The stifling was done for 15 minutes while maintaining the temperature and there was confirmed a precipitate of lithio species. A dry ice which was passed-through absolute diethylether was put-in thereto and the temperature was returned to the room temperature by spending overnight. A solid substance was obtained depending on filtration and thereafter, washing was done by diethylether. The obtained solid substance was dissolved into alkaline water and the water layer was washed by diethylether. The water layer was added with 3M HCl so as to be acidified and extraction was done by diethylether. The diethylether layer was dried by anhydrous magnesium sulfate and by vacuum-distillizing the solvent, there was obtained tetrathiafulvalene-2-carboxylic acid (0.8023 g, 3.23 mmol, 65%) of a red colored solid substance.

$^1$H NMR (DMSO): δ=7.67 (s, 1H), 6.75 (s, 2H) ppm.
IR (KBr): 3060, 2930, 1650, 1530, 1420, 1290 cm$^{-1}$.

Preparation of Ammonium Tetrathiafulvalene-2-carboxylic Acid Salt

Tetrathiafulvalene-2-carboxylic acid (150 mg, 0.604 mmol) was dissolved into absolute diethylether (30 ml) and insoluble components were removed depending on suction filtration. A 28% aqueous ammonia solution was dropped onto the filtrate and a solid substance was separated out by spending 15 seconds on a super sonic wave generation apparatus. The separated-out solid substance was filtrated, washed by diethylether and further, was stirred while being suspended in toluene (3 ml) and thereafter, by filtrating, there was obtained an ammonium tetrathiafulvalene-2-carboxylic acid salt (130.8 mg, 0.493 mmol, 82%).

$^1$H NMR (DMSO): δ=6.75 (s, 2H), 7.67 (s, 1H) ppm.
IR (KBr): 2930, 1650, 1530, 1420, 1290 cm$^{-1}$.
Anal. Calcd. for $C_7H_6NO_2S_4$: C, 31.68; H, 2.66; N, 5.28. Found. C, 31.59; H, 2.75; N, 5.10.

Synthesis of 1-(dibenzotetrathiafulvalene-2-yl)Ethylamine 1,3-benzodithiol-2-thione Isoamylalcohol (0.80 ml, 0.73 mmol), carbon disulfide (4.0 ml, 6.6 mmol), 1,2-dichloroethane (20 ml) and isoamylnitrile (0.97 ml, 0.73 mmol) were added into an argon substituted 100 ml flask, and while heating and stirring, anthranilic acid (1.00 g, 7.30 mmol) which was dissolved into 1,4-dioxane (4 ml) was added thereto. After it was heated to reflux for 10 hours, the reaction was stopped by adding water thereto, a 3M aqueous potassium hydroxide solution was added thereto, extraction was done by dichloromethane, and there was obtained a 1.29 g brown colored liquid by drying & concentrating. Subsequently, starting point components were removed by silica gel column chromatography. Sulfur (0.143 g, 4.46 mmol) and orthodichlorobenzene (2.0 ml) were added thereto and it was heated to reflux for 4 hours. This was left untreated overnight and by filtrating the generated crystal, there was obtained 1,3-benzodithiol-2-thione (0.383 g, 2.08 mmol, 51%) of a brown colored needle shaped crystal.

$^1$H NMR (CDCl$_3$): δ=7.26-7.42 (m, 2H), 7.46-7.50 (m, 2H) ppm.
IR (KBr): 1434, 1264, 1119, 1059, 1025, 741, 474, 892 cm$^{-1}$.

4,5-dimethyl-1,3-dithiol-2-one

A solution in which distilled & purified ethyl methyl ketone (0.53 mg, 5.9 mmol) was dissolved into acetonitrile (8 ml) was added by an amount of 30 ml in a flask under an argon atmosphere and while stirring at room temperature, bromotetramethylsilane (0.86 ml, 6.2 mmol) and distilled & purified dimethyl-sulfoxide (0.46 ml, 6.5 mmol) were added thereto, and it was stirred on an ice bath for one hour. Potassium isopropylxanthogenate (1.14 g, 6.53 mmol) was added thereto and further, it was stirred at room temperature for one hour. Reaction was stopped by adding water, 1M hydrochloric acid was added thereto, extraction was done by diethylether, and drying and concentration were carried out. The concentrate was dissolved into a chloroform/ether (1:1) solution (8 ml) and while stifling it in a 50 ml flask, a 60% aqueous perchloric acid solution (2 ml) was dropped thereto, and after finishing the drops, it was heated to reflux for one hour. Reaction was stopped by adding water, extraction was done by diethylether, and drying and concentration were carried out. By purifying the obtained solid substance by silica gel column chromatography (hexane→hexane/dichloromethane (3:1)), there was obtained 4,5-dimethyl-1,3-dithiol-2-one (0.37 g, 2.5 mmol, 43%) of a colorless crystal.

$^1$H NMR (CDCl$_3$): δ=2.15 (s, 6H) ppm.
IR (KBr): 1655, 1600, 1438, 1188, 1092, 885, 755, 418 cm$^{-1}$.

5-acetyl-1,3-benzodithiol-2-one

A carbon tetrachloride (18 ml) solution of 4,5-dimethyl-1,3-dithiol-2-one (0.445 g, 3.04 mmol) was added into a 50 ml flask under an argon atmosphere and stirred, and N-bromosuccinimide (NBS) (2.38 g, 13.4 mmol) was added hereto. It was heated to reflux for 10 hours under illumination of a filament lamp and thereafter, stirring was done for 13.5 hours at room temperature. The reaction liquid was filtrated and by concentrating & drying-hardening and drying the filtrate, there was obtained a 1.26 g black colored solid substance (crude yield: 107%). The obtained black colored solid substance and tetrabutylammonium iodide (2.34 g, 9.09 mmol) were added into a 50 ml flask, were heated to reflux for 5 hours by being dissolved into acetonitrile (14 ml), and methyl vinyl ketone (1.93 ml, 12.7 mmol) was dropped hereto and thereafter, it was heated to reflux for 30 minutes. After concentration, the obtained solid substance was purified by silica gel column chromatography (dichloromethane/hexane (1:1) →(4:3)) and there was obtained 5-acetyl-1,3-benzodithiol-2-one (0.222 g, 1.06 mmol, 39%).

$^1$H NMR (CDCl$_3$): δ=2.63 (s, 3H), 7.60 (d, 1H, J=4.2 Hz), 7.90 (dd, 1H, J=1.7 Hz, J=3.3 Hz), 8.09 (d, 1H, J=1.2 Hz) ppm.
IR (KBr): 3078, 2923, 1687, 1638, 1391, 1355, 1273, 1248, 889, 818 cm$^{-1}$.

5-(2-methyl-1,3-diodioxarane2-yl)-1,3-benzodithiol-2-one

A toluene (12 ml) solution of 5-acetyl-1,3-benzodithiol-2-one (0.222 g, 1.06 mmol) was added into an argon substituted 50 ml flask and stirred, para-toluenesulfonic acid-hydrate (0.059 g, 0.34 mmol) was added thereto and further, ethylene glycol (0.3 ml) was added and it was heated to reflux for 4 hours. Thereafter, the reaction was stopped by adding triethylamine of around 1.5 ml and further, it was stirred for one hour at room temperature. By concentrating and drying the reaction liquid, there was obtained a 0.359 g brown colored oil. This was purified by silica gel column chromatography (dichloromethane/hexane (2:1)→only dichloromethane) and there was obtained 5-(2-methyl-1,3-diodioxarane2-yl)-1,3-benzodithiol-2-one (0.158 g, 0.621 mmol, 59%).

$^1$H NMR (CDCl$_3$): δ=1.66 (s, 3H), 3.76-3.81 (m, 2H), 4.04-4.09 (m, 2H), 7.45 (s, 2H), 7.63 (s, 1H) ppm.
IR (KBr): 3421, 1685, 1638, 1375, 1274, 1243, 1195, 1038, 878 cm$^{-1}$.

2-acetyldibenzotetrathiafulvalene 1,3-benzodithiol-2-thione (1.19 g, 6.46 mmol), 5-(2-methyl-1,3-diodioxarane2-yl)-1,3-benzodithiol-2-one (0.66 g, 2.60 mmol) and triethylphosphite (70 ml) were added into an argon substituted 200 ml flask, and it was heated to reflux for 9 hours. Water was added and while cooling by an ice bath, 3M hydrochloric acid was dropped and thereafter, concentration and drying were carried out. The product was purified by silica gel column chromatography and thereafter, by executing recrystallization from chloroform (only chloroform→only ethylacetate), there was obtained 2-acetyldibenzotetrathiafulvalene (0.481 g, 1.39 mmol, 53%).

$^1$H NMR (CDCl$_3$): δ=2.57 (s, 3H), 7.12-7.15 (m, 2H), 7.26-7.33 (m, 2H), 7.69 (dd, 2H, J=3.5 Hz, J=0.6 Hz), 7.83 (d, 1H, J=0.8 Hz) ppm.
IR (KBr): 1668, 1568, 1447, 1390, 1348, 1272, 1235, 1121, 810, 748 cm$^{-1}$.

O-methyl-2-acetyldibenzotetrathiafulvaleneoxime 2-acetyldibenzotetrathiafulvalene (0.98 g, 2.83 mmol) was added into a 200 ml flask and stirred by adding pyridine (70 ml), O-methylhydroxyamine hydrochloric acid salt (0.354, 4.24 mmol) was added hereto, and it was heated to reflux for 6 hours and stirred for 40 hours at room temperature. Water was added to the reaction liquid and extraction was done by dichloromethane, the organic layer was concentrated and dried, the product thereof was recrystallized by chloroform, and there was obtained O-methyl-2-acetyldibenzotetrathiafulvaleneoxime (0.85 g, 2.26 mmol, 80%).

$^1$H NMR (CDCl$_3$): δ=2.17 (d, 3H, E/Z mixture), 3.98 (d, 3H, E/Z mixture), 7.10-7.13 (m, 2H), 7.21-7.27 (m, 5H), 7.38 (d, 1H, J=4.2 Hz), 7.58 (d, 1H, E/Z mixture) ppm.
IR (KBr): 3436, 2923, 1653, 1444, 1050, 892, 818, 745 cm$^{-1}$.

1-(dibenzotetrathiafulvalene-2-yl)Ethylamine

O-methyl-2-acetyldibenzotetrathiafulvaleneoxime (1.92 g, 5.12 mmol) and THF (160 ml) were added into an argon substituted 300 ml flask and stirred, a boranetetrahydrofuran complex tetrahydrofuran solution (21.1 ml, 21.4 mmol) was added under an ice-cold condition, and it was heated to reflux for 3 hours. The reaction was stopped by adding 1M hydrochloric acid (20 ml) to the cooled reaction liquid, an aqueous potassium hydroxide solution was added small amount by small amount, concurrently, concentration was carried out so as to remove THF for a certain amount thereof and thereafter, the liquid-property was made to be in basicity and extraction was done by dichloromethane. By concentrating and drying the organic layer, there was obtained 1-(dibenzotetrathiafulvalene-2-yl)-ethylamine (1.67 g, 4.79 mmol, 94%).

$^1$H NMR (CDCl$_3$): δ=1.35 (d, 3H, J=3.3 Hz), 4.08 (q, 1H, J=3.3 Hz), 7.08-7.14 (m, 3H), 7.19-7.29 (m, 4H) ppm.
IR (KBr): 3046, 2922, 1561, 1445, 1428, 1260, 1120, 1028, 811, 776, 737 cm$^{-1}$.

(Preparation of Brønsted Acid Salt)

Salts with various kinds of acids were prepared by dissolving 1-(dibenzotetrathiafulvalene-2-yl)ethylamine into a solvent (diethylether or dichloromethane), dropping an Aqueous Brønsted acid solution (HBr, HBF$_4$) thereto, applying a super sonic wave for few minutes and filtrating the produced solid substance. Distilled water used for the washing one time was 2 or 3 droplets by a Pasteur pipette and the washing was completed by executing that action around five times.

1-(dibenzotetrathiafulvalene-2-yl)Ethylamine-Bromic Acid Salt $^1$H NMR (DMSO-d6): δ=1.49 (d, 3H, J=6.9 Hz), 4.40 (s, 1H), 7.27-7.76 (m, 7H), 8.21 (s, 3H) ppm.

IR (KBr): 2923, 1590, 1497, 1444, 1222, 1080, 738, 591, 435 cm$^{-1}$.

Anal. Calcd. for $C_{16}H_{14}BrNS_4$—$H_2O$: C, 43.03%; H, 3.62%; N, 3.14%. Found. C, 43.24%; H, 3.37%, N, 3.04%.

1-(dibenzotetrathiafulvalene-2-yl)Ethylamine-Boron Tetrafluoride Salt $^1$H NMR (DMSO-d6): δ=1.50 (d, 3H, J=6.9 Hz), 4.39 (q, 1H, J=6.9 Hz), 7.33 (m, 4H), 7.62 (m, 5H) ppm.

IR (KBr): 2924, 1616, 1498, 1445, 1225, 1083, 741, 591, 523, 415 cm$^{-1}$.

Anal. Calcd. for $C_{16}H_{14}BF_4NS_4$: C, 44.14%; H, 3.24%; N, 3.22%. Found. C, 43.96%; H, 3.40%, N, 3.17%.

[Use Application]

The compound mentioned above presents an electronic material property different from that of a general organic conductor. For example, a high hall coefficient is presented and the value thereof is the highest level among the levels of the materials which were known until now as those having high hall coefficients. Consequently, it is conceivable that the compound mentioned above will be applied to a high sensitive magnetic field sensor and a hall element.

Also, a high thermal electromotive force is presented and the value thereof is in a top class among those of inorganic substances. Consequently, it is conceivable that the compound mentioned above will be applied also to an exhaust heat conversion material and a solar cell.

The electrical conductivity thereof is in a comparable level as that of a usual organic semiconductor. Consequently, applications to a driving device of a display, an organic EL and an application to a device are also conceivable.

In particular, a high material property value is presented in a state of not a single crystal but of a microcrystal pressure forming, so that there can be suggested a possibility in which form-conversion to polymer or liquid crystal is executed and thin-film forming can be accomplished. Thin film forming by coating application is to open up possibilities toward a lot of use applications.

The technique mentioned above is based on a general principle which does not choose a processing mode, so that there is a possibility for the industrial utilization value thereof to exceed that of the inorganic Si-based amorphous.

It should be noted that there can be cited, for the examples of the use applications, such as a diode joining (PN-joining) a P type semiconductor and an N type semiconductor, a transistor in which an N type semiconductor is sandwiched by P type semiconductors or in which a P type semiconductor is sandwiched by N type semiconductors, a solar cell or an integrated circuit (IC/LSI) designed by using a PN junction, and the like. In addition, there can be also cited, for the examples of the use applications, electronic apparatuses of a computer and the like which have semiconductor devices such as electric products (electronic apparatuses) referred to as a television receiver, a mobile phone, a computer and the like and also an automobile, various kinds of industrial apparatuses, and the like.

In particular, an application as an organic thin film solar cell and also, applications to polymerization, liquid crystallization and the like by converting a donor molecule for a functional group are promising.

SUMMARY

In the method mentioned above, it is possible to produce an organic semiconductor purposively by salt-forming a very simple donor organic molecule with an inorganic acid or an inorganic base by 1:1. In this technique, it is possible to obtain a stabilized organic semiconductor even without executing a doping.

Also, in the system mentioned above, there is provided a compound having features in which differently from a usual organic crystal, conductivity is expressed without relying upon the processing mode and also, in which differently from a doped polymer, a chemically stable characteristic and a characteristic of not being deteriorated easily are obtained (it was confirmed that also the sample for which 3 years passed after the synthesis at room temperature & under existence of air has identical performance as that at the time of synthesis).

Based on a fact that the regularity derived from the hydrogen bonding network is maintained to a certain degree in an organic solid, the conduction molecules are not random perfectly and there remains regularity of arrangement therein. It is conceivable that this fact will increase charge separation capability between a conduction electron which becomes a carrier and a positive hole. This shows that there is possibility of obtaining an effect of stimulating improvement of energy conversion efficiency, which is assumed to be the largest problem in an organic solar cell, by the use of the compound mentioned above.

Further, according to the method mentioned above, it is possible to obtain a high purity organic semiconductor simply only by forming a 1:1 salt between a donor molecule for which a hydrogen bonding functional group was introduced and an inorganic acid or an inorganic base.

Also, in this system, differently from a general charge transfer complex, an acceptor molecule is not always needed.

In particular, the compound mentioned above is an organic-ion/inorganic-ion salt, so that it is chemically stable and it exists stably if, for example, the heating is until 100° C.

A lot of candidate compounds which express similar effects are conceivable.

In this manner, the present exemplified embodiment is to provide a foundational knowledge when designing a new material in which many functions are controllable.

[Patent-Right Interpretation or the Like]

As described above, it has been explained with respect to the present invention while referring to specific exemplified embodiments. However, it is obvious that a person skilled in the art can achieve a modification or a substitution of the exemplified embodiment in a scope without departing from the gist of the present invention. More specifically, the present invention has been disclosed in a form referred to as illustrative embodiments and the described contents of the present specification should not be interpreted limitedly. In order to judge the gist of the present invention, the columns of the patent claims described in the beginning should be taken into consideration.

Also, it is clear that the exemplified embodiments for the explanation of this invention achieve the objects mentioned above, but it is to be understood that it is also possible for a person skilled in the art to employ many modifications and other embodiments. It is also allowed for the element or the component of the patent claims, of the specification, of the drawings and of each exemplified embodiment for the explanation to be employed together with another one or a combination thereof. The patent claims are intended to cover also such modifications and other exemplified embodiments in the scope thereof, and these are covered in the technical idea and the technical scope of this invention.

INDUSTRIAL APPLICABILITY

The compound mentioned above presents an electronic material property different from that of a general organic conductor. For example, a high hall coefficient is presented and the value thereof is the highest level among the levels of the materials which were known until now as those having high hall coefficients. Consequently, it is conceivable that the compound mentioned above will be applied to a high sensitive magnetic field sensor, a hall element and the like.

The invention claimed is:

1. An organic compound, characterized by being any one of the compounds expressed by the following Chemical Formulas 1:

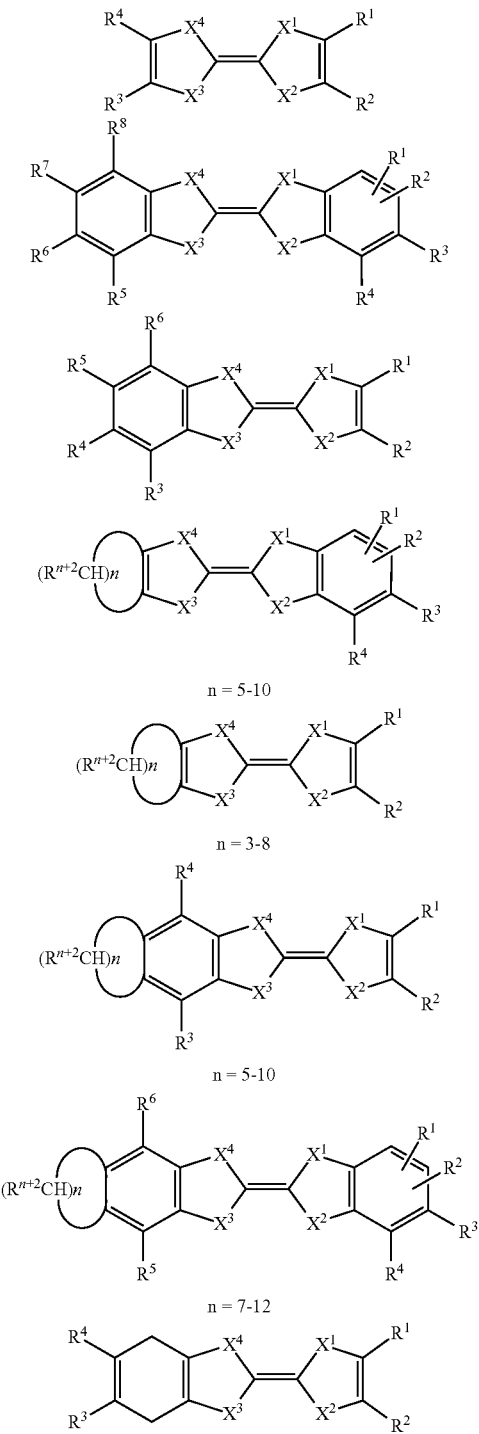

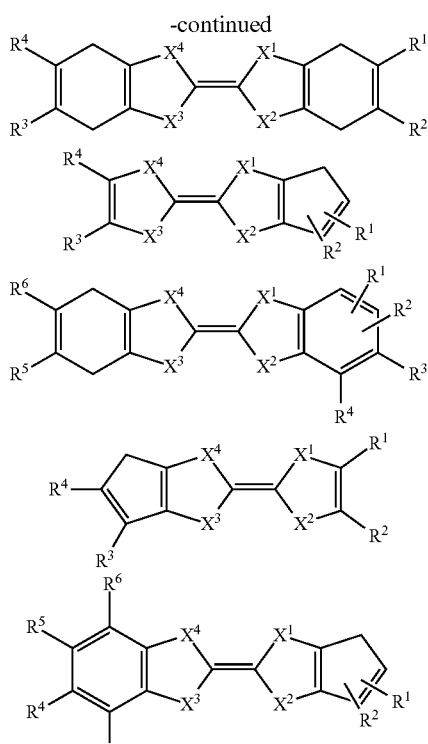

in the formulas, $X^1$ to $X^4$ are Se, and $R^1$ is any one expressed in the following Chemical Formulas 2:

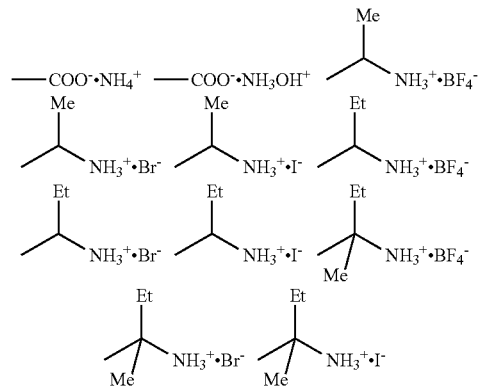

and $R^2$ to $R^8$ in the Chemical Formulas 1 are independently one of Chemical Formulas 3:

H, $ClHm$ ($l = 1\sim30$, $m = 3\sim61$), $SClHm$ ($l = 1\sim30$, $m = 3\sim61$), $OClHm$ ($l = 1\sim30$, $m = 3\sim61$), $S(CH_2S)lCH_3$ ($l = 1\sim20$)

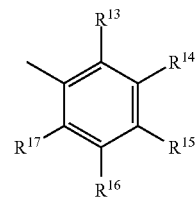

$R^{13}\sim R^{17}$ = H, $ClHm$ ($l = 1\sim30$, $m = 3\sim61$), $SClHm$ ($l = 1\sim30$, $m = 3\sim61$), $OClHm$ ($l = 1\sim30$, $m = 3\sim61$), $S(CH_2S)lCH_3$ ($l = 1\sim20$)

-continued

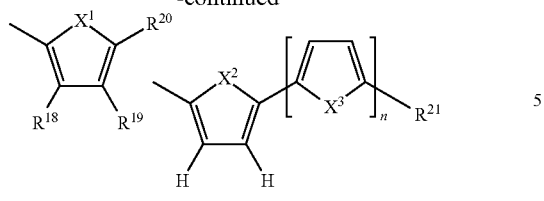

n = 1~50
$R^{18}$~$R^{21}$ = H, $C_lH_m$ (l = 1~30, m = 3~61), $SC_lH_m$ (l = 1~30, m = 3~61), $OC_lH_m$ (l = 1~30, m = 3~61), $S(CH_2S)_lCH_3$ (l = 1~20)

and wherein the organic compound has an electrical conductivity of about $10^2$ to about $10^{-6}$ S/cm.

2. A semiconductor comprising the organic compound according to claim 1.

3. A semiconductor device comprising, the organic compound according to claim 1.

4. A solar cell, comprising the organic compound according to claim 2.

* * * * *